United States Patent
Bernard et al.

(10) Patent No.: US 8,506,511 B2
(45) Date of Patent: Aug. 13, 2013

(54) METHOD AND DEVICE FOR REMOVAL OF RADIOCONTRAST MEDIA FROM BLOOD

(75) Inventors: Steven J. Bernard, Andover, MN (US); John J. O'Mahony, Minnetonka, MN (US); Andrew V. Halpert, Coral Springs, FL (US); Mark Gelfand, New York, NY (US); Howard R. Levin, Teaneck, NJ (US)

(73) Assignee: Gambro UF Solutions, Inc., Brooklyn Park, MN (US)

( * ) Notice: Subject to any disclaimer, the term of this patent is extended or adjusted under 35 U.S.C. 154(b) by 663 days.

(21) Appl. No.: 11/620,438

(22) Filed: Jan. 5, 2007

(65) Prior Publication Data
US 2007/0123838 A1 May 31, 2007

Related U.S. Application Data

(60) Division of application No. 10/653,100, filed on Sep. 3, 2003, now Pat. No. 7,163,520, which is a continuation-in-part of application No. 10/606,365, filed on Jun. 26, 2003, now abandoned.

(60) Provisional application No. 60/391,413, filed on Jun. 26, 2002.

(51) Int. Cl.
*A61M 1/38* (2006.01)

(52) U.S. Cl.
USPC ........................... 604/5.04; 604/5.01

(58) Field of Classification Search
USPC .............. 604/500, 506, 507, 508, 8; 210/646
See application file for complete search history.

(56) References Cited

U.S. PATENT DOCUMENTS

| 4,204,957 A * | 5/1980 | Weickhardt ............... 210/98 |
| 4,469,593 A * | 9/1984 | Ishihara et al. ............ 210/96.2 |
| 4,952,127 A * | 8/1990 | Schmeisser et al. ........... 494/1 |
| 5,817,046 A | 10/1998 | Glickman |
| 6,471,872 B2 * | 10/2002 | Kitaevich et al. ........... 210/739 |
| 6,554,819 B2 | 4/2003 | Reich |
| 6,780,322 B1 * | 8/2004 | Bissler et al. ............... 210/637 |
| 6,955,655 B2 * | 10/2005 | Burbank et al. ............. 604/5.01 |
| 2002/0091349 A1 | 7/2002 | Reich |

(Continued)

FOREIGN PATENT DOCUMENTS
EP              832656 A1 * 4/1998
WO   WO 2006090706 A1 * 2/2006

Primary Examiner — Susan Su
(74) Attorney, Agent, or Firm — Nixon & Vanderhye P.C.

(57) ABSTRACT

An extracorporeal blood circuit including: a withdrawal conduit connectable to a coronary withdrawal catheter; a withdrawal pump connectable to the withdrawal conduit, wherein a pumping rate of the withdrawal pump determines a blood withdrawal rate from the coronary withdrawal catheter; a filter having an input connected to the withdrawal conduit and a blood output connected to an infusion conduit and a filtrate output connected to a filtrate conduit; a filtrate measurement device to determine an amount of filtrate removed from the blood in the filter; a fluid supplementation conduit providing a blood replacement fluid to at least one of the withdrawal conduit, filter and infusion conduit; a supplementation pump connectable to the fluid supplementation conduit, wherein a pumping rate of the supplementation pump determines a rate at which the blood replacement fluid flows into the blood flowing through the blood circuit, and a controller regulating the pumping rate of the supplementation pump such that the rate of the blood replacement fluid provides an amount of blood replacement fluid to the at least one of the withdrawal conduit, filter and infusion conduit so as to substantially match the amount of filtrate removed.

17 Claims, 15 Drawing Sheets

(56) References Cited

U.S. PATENT DOCUMENTS

| | | |
|---|---|---|
| 2002/0099254 A1 | 7/2002 | Movahed |
| 2003/0120202 A1* | 6/2003 | Gordon ............................ 604/28 |
| 2004/0011740 A1 | 1/2004 | Bernard et al. |
| 2004/0068219 A1* | 4/2004 | Summerton et al. ......... 604/5.01 |
| 2004/0228829 A1* | 11/2004 | Roberts et al. ............... 424/78.1 |
| 2006/0124548 A1* | 6/2006 | Okazaki ......................... 210/646 |
| 2006/0157413 A1* | 7/2006 | Bene et al. ..................... 210/646 |
| 2007/0038191 A1* | 2/2007 | Burbank et al. ............... 604/317 |
| 2007/0215545 A1* | 9/2007 | Bissler et al. ................. 210/646 |
| 2008/0154170 A1* | 6/2008 | Lannoy ........................ 604/6.09 |

* cited by examiner

METHOD AND DEVICE FOR REMOVAL OF RADIOCONTRAST MEDIA FROM BLOOD

RELATED APPLICATION

This is a divisional application of U.S. patent application Ser. No. 10/653,100 (U.S. Pat. No. 7,163,520) filed Sep. 3, 2003, which is a continuation-in-part (CIP) application of U.S. patent application Ser. No. 10/606,365, filed Jun. 26, 2003, and claims priority, under 35 U.S.C. §119(e), to U.S. Provisional Application Ser. No. 60/391,413 filed Jun. 26, 2002, the entirety of each of these applications is incorporated herein by reference.

BACKGROUND OF THE INVENTION

Contrast Nephropathy

The Clinical Problem

With the increasing use of radiographic contrast media in diagnostic and interventional procedures, contrast-induced nephropathy (CN) has become an important cause of acute renal impairment. While CN rarely (less than 1% of cases) results in permanent renal failure, CN in any form, results in a significantly increased overall cost to the hospital from prolonged admissions to observe and/or treat while awaiting the return of the patient's pre-CN baseline renal function.

Even in its milder forms, CN can increase the time that patients remain in the hospital by 3-5 days. The more severe the CN, the longer the increase in hospital stay. In those patients who require short-term dialysis (even though their kidneys eventually return to their pre-CN baseline), the hospital stay made be increased by 2-4 weeks due to CN.

The Properties, Use and Effects of Contrast Media

Radiographic contrast agents can be grouped into two main categories: positive contrast agents and negative contrast agents. Positive contrast media are radiopaque (appearing lighter than surrounding structures) due to their ability to attenuate the X-ray beam. Positive contrast agents contain elements with high atomic weights, (such as iodine, bromine, and barium) which add density to the tissues of interest. Negative contrast agents are radiolucent (darker than surrounding structures) because of their inability to attenuate the X-ray beam. Air and water are examples of negative contrast agents.

Intravenous contrast agents are used to help highlight blood vessels and to enhance the tissue structure of various organs such as the brain, spine, liver and kidneys. Intravenous contrast is clear like water and has a similar consistency. It is typically packaged in glass bottle or vial. A sterile syringe is used to draw it from the bottle or a power injector is used to administer the contrast. Typically between 75 cc to 150 cc (about 2.5 oz. to 5 oz) of contrast is injected depending upon the patient's age, weight, area being imaged and cardiovascular health.

Types of Intravascular Contrast Media

Intravascular contrast agents typically comprise iodinated benzene ring derivatives that are formulated as sodium or megiumine salts. The multiple iodine molecules contained within the contrast agent are responsible for the X-ray attenuation. The amount of radiopacity that is generated by a particular contrast agent is a function of the percentage of iodine in the molecule and the concentration of the contrast media administered. The iodine content in different radiographic contrast media can vary from 11% to 48%.). Iodinated contrast agents are classified as ionic or high osmolar contrast media (HOCM) or nonionic or low osmolar contrast media (LOCM).

Ionic (HOCM)

Ionic contrast media dissociate into separate particles, or ions, when placed in water solutions. An ion is an atom or group of atoms that carries a positive or negative charge. The dissociation of the molecules in ionic contrast media is responsible for its increased osmolality in the blood in comparison to nonionic contrast media. Ionic media breakdown into cations, positively charged particles and anions, negatively charged particles. For every three iodine molecules present in an ionic media, one cation and one anion are produced when it enters a solution. Ionic contrast media are generally referred to as 3:2 compounds. The cations and anions are the direct result of the disassociation of compounds that are attached as "side chains" to the contrast media molecule. Sodium and/or meglumine are cations and diatrizoate and iothalamate are the common anions. Human blood has an osmolality of approximately 300 milliosmoles (mOsm) per kilogram (kg) or 30 mOsm per deciliter (or 30%), while a typical ionic contrast agent can have an osmolality on the order of 1300 mOsm/kg to 1600 mOsm/kg or 130 mOsm per deciliter, making it a hypertonic solution with respect to blood.

Nonionic (LOCM)

Unlike ionic contrast media, the nonionic contrast media do not dissociate into ions, thus resulting in a lower osmolality contrast agent. Non-ionic contrast media do not dissolve into charged particles when it enters a solution. For every three iodine molecules in a non-ionic solution, one neutral molecule is produced. Non-ionic contrast media are referred to as 3:1 compounds. Typical nonionic contrast agents have an osmolality on the order of 500 mOsm/kg to 850 mOsm/kg or 50 mOsm per deciliter to 85 mOsm per deciliter. Although their osmolality is lower than ionic contrast media, they are still considered hypertonic with respect to blood.

The low-osmolality contrast media are represented structurally by the ionic dimers, nonionic monomers, and nonionic dimers. Ioxaglate is the only commonly used ionic dimer. In solution it forms two particle aggregates and does not readily ionize, rendering an osmolality of about 600 mOsm/kg H2O. The nonionic monomers, as a result of their lower toxicities, are rapidly becoming the contrast agents of choice. In addition to nonionic tendencies and lower osmolalities, the newer nonionic monomers, such as ioversol and iohexal, are more hydrophilic and thus potentially less chemotoxic. The approximate osmolality range of these agents is 290 to 860 mOsm/kg H2O. The lower toxicity of LOCM is offset somewhat by higher cost. The nonionic dimers are largely in the developmental stages. Although the osmolality of these agents approaches that of plasma, they are highly viscous and thus of limited clinical usefulness. When evaluating the literature, one must note the potential differences in the terms ionic, nonionic, and low osmolality, high osmolality. Ioxaglate is an LOCM, but it also has some ionic tendencies.

The osmolality of a solution is the measurement of the number of molecules and particles in a solution per kilogram of water. An injection of contrast media, especially ionic HOCM, results in a big increase in the number of particles contained in the vascular system. The introduction of contrast media into the vascular system causes water from intracellular place to move into the intravascular space in an attempt to equalize concentrations. The blood vessels dilate in an attempt to compensate from the increased fluid volume. If the fluid shift is too large, fluid will transudates into the surrounding tissues resulting is such conditions as pulmonary edema.

How is Intravenous Contrast Used

An intravenous needle is first placed into a vein in the hand or arm. Once the needle is in place, the vein is flushed with saline solution. The contrast may be hand injected using a large syringe connected to the needle via tubing or via a power-assisted injector. After the iodine contrast has been injected, e.g., as a bolus, into the blood stream, it circulates through the heart and passes into the arteries, through the body's capillaries and then into the veins and back to the heart. The x-ray beam is attenuated as they pass through the blood vessels and organs containing contrast. This causes the blood vessels and organs filled with the contrast to "enhance" and show up as white areas on the x-ray or CT (computed tomography) images. The kidneys and liver eliminate the contrast from the blood.

There are three phases of intravascular contrast enhancement: bolus or arterial phase, non-equilibrium or venous phase, and the equilibrium or portal phase. The bolus phase represents the critical time of peak enhancement within the target vessel or organ and occurs immediately after the injection of contrast and lasts between 10 seconds and 60 seconds postinfusion depending on the amount and site of injection. For coronary angiography, a 5 cc bolus into the coronary artery will last much shorter than a 70 cc bolus into the left ventricle. The non-equilibrium phase occurs approximately 1 minute after the bolus of contrast media. The last phase is considered the equilibrium phase, which occurs approximately 2 minutes after the bolus injection. Thus, contrast becomes equally distributed in the total blood volume by about 2 minutes after a single injection.

On average, people at increased risk for contrast nephropathy receive less iodinated contrast material that those with normal renal function. The amount ranges from 250-300 cc in minimal to moderate renal insufficiency to as little as 50-70 cc in the highest risk patients.

Toxicity of Contrast Media

The toxicity of iodinated radiographic contrast media is related to (1) chemotoxicity, (2) ion toxicity, and (3) osmotoxicity of the specific compound used. Chemotoxicity increases as the hydrophobic nature of the substance increases. Chemotoxicity can result in release of vasoactive substances, activation of the complement and fibrinolytic systems, blockage of platelet aggregation, direct neurotoxicity, and decreased myocardial contractility and conduction. Ion toxicity is due to the direct effects of the anionic contrast medium or its conjugated cation on cellular membranes or cellular function. Osmotoxicity can result in pain upon injection, blood-brain barrier disruption, vagal and emetic center stimulation, decreased myocardial contractility, lowering of the myocardial fibrillation threshold, renal vasoconstriction, erythrocyte cell wall rigidity, increased pulmonary artery pressure, and decreased peripheral vascular resistance and vasodilation.

The so-called allergic reaction to iodinated radiographic contrast media is, in fact, an anaphylactoid or pseudoallergic reaction. Numerous mediators typical of allergic reactions are released or activated, but the mechanism is not antigen-antibody mediated. A true antibody-mediated reaction to iodinated radiographic contrast media is rare, with only three reported cases as of 1994. The exact mechanisms of these anaphylactoid reactions are not known but probably include direct cellular effects, direct enzyme induction, and direct activation of the compliment, fibrinolytic, kinin, and other systems. Symptoms usually develop within minutes of administration and reflect the actions of the released or activated mediating substances.

Potential Mechanisms of Contrast Nephropathy

The mechanisms of contrast nephropathy (CN) are not well understood. However, CN appears to be the result of a synergistic combination of direct renal tubular epithelial cell toxicity and renal medullary ischemia.

The injection of contrast induces a biphasic hemodynamic change in the kidney, with an initial, transient increase and then a more prolonged decrease in renal blood flow. Normal renal blood flow usually returns within 1 to 2 hours. The initial increased osmotic load of the contrast media triggers an intrarenal feedback resulting in renal arteriolar vasoconstriction. This phenomena is enhanced in salt-depleted or dehydrated animals. The mediators of these changes are still unknown. The renin-angiotensin system, calcium, prostaglandin, nitric oxide, endothelin and adenosine have been identified as possible mediators of this vasoconstriction.

Direct cytotoxicity in CN is suggested by histologic changes of cell injury and enzymuria after contrast administration. The nature of the contrast, associated ions, concentration, and concomitant hypoxia are all important to the degree of cellular damage, while the osmolality of the solution seems to be of secondary importance.

Definition and Clinical Features of CN

Renal dysfunction has been long recognized to be associated with the use of radiographic contrast media. The spectrum of dysfunction ranges from a transient slight increase in serum creatinine levels to overt renal failure requiring transient or long-term dialysis. Multiple definitions of CN, variations in the length of time serum creatinine is monitored, the different types, doses, and routes of contrast media used; and varying study designs have all resulted in a wide range of results and often conflicting conclusions and recommendations.

Mild, transient decreases in GFR occur after contrast administration in almost all patients. Whether a patient develops clinically significant acute renal failure, however, depends very much on the presence or absence of certain risk factors. Baseline renal impairment, diabetes mellitus, congestive heart failure, and higher doses of contrast media increase the risk of CN. Other risk factors include reduced effective arterial volume (e.g., due to dehydration, nephrosis, cirrhosis) or concurrent use of potentially nephrotoxic drugs such as nonsteroidal anti-inflammatory agents and angiotensin-converting enzyme inhibitors. Of all these risk factors, preexisting renal impairment appears to be the single most important; patients with diabetes mellitus and renal impairment, however, have a substantially higher risk of CN than patients with renal impairment alone.

Though many different definitions of CN appear in the literature, but it is commonly defined as an acute decline in renal function following the administration of intravenous contrast in the absence of other causes. Contrast nephropathy is commonly defined as the rise of 25% or more from the patient's baseline creatinine or a rise of at least 0.5 mg/dl. Patients with CN typically present with an acute rise in serum creatinine anywhere from 24 to 48 hours after the contrast study. Serum creatinine generally peaks at 3 to 5 days and returns to baseline value by 7 to 10 days.

The acute renal failure is nonoliguric in most cases. Urinalysis often reveals granular casts, tubular epithelial cells, and minimal proteinuria, but in many cases may be entirely bland. Most, but not all, patients exhibit low fractional excretion of sodium. The diagnosis of CN is frequently obvious if the typical course of events follows the administration of contrast. However, other causes of acute renal failure, including atheromatous embolic disease, ischemia, and other nephrotoxins should always be considered. This is particularly true if significant renal impairment should occur in patients without risk factors for CN.

Incidence of CN

Prospective studies have produced extremely varied estimates of the incidence of CN. These discrepancies are due to differences in the definition of renal failure as well as differences in patient comorbidity and the presence of other potential causes of acute renal failure. A recent epidemiologic study reported a rate of 14.5% in a series of approximately 1,800 consecutive patients undergoing invasive cardiac procedures. Patients without any significant risk factors have a much lower risk, averaging about 3% in prospective studies. On the other hand, the risk of renal failure after contrast rises with the number of risk factors present. In one study, the frequency of renal failure rose progressively from 1.2 to 100% as the number of risk factors went from zero to four.

Clinical Outcomes

The clinical importance of CN may not be immediately obvious given the high frequency of recovery of renal function, but it is by no means a benign complication. CN is no different from acute renal failure of any other etiology in terms of the complications that may ensue. Dialysis is infrequently required in approximately 0.7% of patients. Those who do require dialysis have very bad outcomes with a high mortality. Patients who don't require dialysis may still have increase in creatinine to 4-5 mg/dl. This reduction in renal function is clinically significant and may result in increase morbidity and mortality from delays in definitive therapies (such as coronary artery bypass surgery), need for alteration or increased toxicity of medications, delays in important diagnostic tests and longer total hospital stays. In addition, some degree of residual renal impairment has been reported in as many as 30% of those affected by CN. Other comorbid events such as hypotension, sepsis, and atheroembolic disease certainly contribute. Finally, there is some evidence that mortality may be increased in patients with CN. In a retrospective study, Levy et al. compared the outcomes of hospitalized patients with CN to a control group of patients matched for age, baseline serum creatinine, and type of diagnostic procedure that received contrast but did not develop CN. The mortality in the CN group was 34% compared with 7% in the control group ($P<0.001$, odds ratio 5.5), even when severity of comorbid illness was controlled by matching patients by APACHE II scores.

Previous Strategies Used to Prevent Contrast Nephropathy

Contrast administration, more often than not, is a planned procedure, and patients at particularly high risk can often be identified before the investigation. Renal impairment may be asymptomatic until advanced, but it is impractical to measure renal function before contrast administration in all cases. If no other risk factors for renal impairment are present, renal function is generally not assessed pre-study. When contrast administration is deemed appropriate, the lowest dose of contrast possible should be used. Optimally, any risk factors for CN should be corrected before contrast administration. If contrast must be administered in the presence of an uncorrectable or uncorrected risk factor, it is advisable to monitor renal function by serum creatinine before and at 48 to 72 h after the procedure.

A variety of specific measures have been used in an attempt to decrease the risk of CN, particularly in high-risk patients. The following is a discussion of the evidence supporting the use of some of the more common practices.

Fluid Administration

The administration of intravenous fluids has long been used to reduce the likelihood of CN for high-risk patients. The rationale for this approach is that giving fluids before the study may correct subclinical dehydration, whereas hydration for a period of time afterward may counter an osmotic diuresis resulting from the contrast. It is clear that even vigorous fluid administration does not afford complete protection from CN for high-risk patients. Even if only modestly beneficial, however, this approach is simple and carries minimal risks of adverse effects if appropriate care is taken, e.g., close monitoring of the patient's fluid balance and clinical status. However, use of this method in patients with Congestive Heart Failure or other fluid overload states in impractical.

Furosemide

The use of furosemide as prophylaxis for CN has been controversial. It has been hypothesized that loop diuretics might reduce the potential for ischemic injury by interfering with active transport and decreasing the oxygen demands of medullary tubular segments. Recent studies, however, suggest that furosemide may actually be detrimental in certain patients. There is currently more evidence arguing against rather than for the use of furosemide for the prophylaxis of CN, and its use for this purpose is not generally recommended.

Mannitol

Infusions of mannitol have also been widely used to prevent CN, but again its use is controversial. Overall, there is not enough evidence to recommend mannitol as a means to reduce CN.

Dopamine

Low-dose dopamine is a renal vasodilator and is effective even in patients with chronic renal insufficiency. This property has made it very attractive as a potential means for preventing CN, but clinical studies thus far have shown mixed results. Although it appears that dopamine may be of some benefit in preventing CN in nondiabetic patients, more evidence is required before it can be recommended for routine use. Dopamine should not be used to prevent CN in diabetic patients.

Atrial Natriuretic Peptide

Atrial natriuretic peptide (ANP) may theoretically interfere with the pathogenesis of CN by increasing renal blood flow, but clinical studies have not yet shown such a benefit. Based on available evidence, ANP cannot be recommended for prophylaxis of CN.

Calcium Channel Blockers

Drugs of this class have been shown to blunt the decreases in renal blood flow induced by contrast in laboratory studies. Several randomized trials of calcium-blocking agents for the prevention of CN have been published. However, the studies are quite small and do not include high-risk patients with renal insufficiency. Additional large-scale randomized trials are necessary, particularly in high-risk patients, before calcium channel blockers can be recommended for the prevention of CN. Patients taking calcium channel blockers for other indications, however, should continue their therapy uninterrupted.

Theophylline

Because adenosine has been suggested as having a role in the pathogenesis of CN, theophylline, an adenosine antagonist, has been investigated as a means to reduce the risk of this complication. Some studies have suggested that theophylline prevents some of the contrast-associated changes in renal function, but a benefit over saline hydration alone has not been convincingly demonstrated. This is particularly true with respect to patients with preexisting renal impairment. Nevertheless, there may be some value to the use of theophylline for reduction of CN in those at risk. Although the dose, duration, and route of administration of theophylline differed in each study, it seems likely that a dose of less than 5 mg/kg for less than 2 days, starting before contrast, is appropriate.

Current Strategies to Prevent Contrast Nephropathy

There are at least three current strategies, none of which have shown long-term proven benefit. Mucomyst is a drug that has shown some potential benefit. Iodixenol is purported to be a less toxic contrast agent though it is likely to be only an incremental benefit on existing diseases. Fenoldopam is a calcium-channel blocker made by Abbott that is supposed to increase renal blood flow. For each of these therapies, little significant clinical benefit has actually been shown. If at least equally effective, drug therapies are always preferred to device therapies. However, if none of these are proven to be clinically helpful, then there is a significant market for a novel device therapy.

Previous Use of Device Therapies to Reduce Contrast Concentrations in Blood

Hemodialysis and hemofiltration (artificial kidney) devices were used clinically in attempt to alter the contrast induced kidney damage. Clinically, these therapies have shown little sustained benefit. It is our belief that the longer the contrast is allowed to act on the kidney, the greater the potential for toxicity. What is not clear is 1) how soon the deleterious effects occur after contrast is injected and 2) whether removal of the contrast once damage has occurred is beneficial.

Some pre-clinical data is available to suggest that the higher the contrast dose and the longer the duration of exposure, the more significant the renal dysfunction. There have been no clinical trials that addressed the issue of essentially complete removal of contrast in less than two hours from the start of the procedure.

In view of the foregoing, there is a long felt need for a medical device that removes radiocontrast agents from the blood of a patient promptly after the injection of the agent. Interventional radiologists and cardiologists will use the technology during cardiac catheterization as well as potentially during other (e.g. AAA stenting, peripheral stenting, CT Scanning, or urology) procedures. There is a recognized problem associated with the use of intravenous radiocontrast medium (contrast) in the catheterization lab known as the radiocontrast induced nephropathy (RCN). Contrast can cause kidney damage. The clinical needs for a device to remove radiocontrast agents are:

1. To reduce the probability and severity of contrast nephropathy in the high-risk group of patients.
2. To allow the cardiologist or radiologist to use contrast more liberally during the procedure therefore making the procedure more effective and fast.
3. To make catheterization available to patients currently rejected because their kidneys are considered high risk.

Ideally the device shall be used by the catheter laboratory staff during the procedure and treatment terminated when the procedure is over. Treatment could continue for another hour after the procedure in the holding area.

The following are examples of the technical obstacles to clinical effective removal of radiocontrast from the bloodstream:

1. Modern nonionic contrast media molecules are small, non polarized and extremely hydrophilic (bind strongly to water). There are number of different chemical configurations. It is difficult to non-specifically separate contrast from plasma water.
2. Contrast media after injection does not stay in the blood but redistributes in the body fluid volume rapidly (within 15-20 minutes 50% redistribution level is reached). Total distribution volume of contrast in an average 70 kg person is on the order of 18-20 liters. In a larger person it can be significantly more. The consequence of this is that, if contrast is not removed before it is redistributed, the volume of body fluid that needs to be cleared of contrast increases from 2.5-3 liters of plasma water to 6 times that much. Since extracorporeal blood treatment can only clear plasma at a certain intrinsic rate, the duration of treatment required to achieve substantial clearance will increase proportionally.
3. Onset of damage to kidneys by contrast is quick. There are reasons to believe that some ischemic damage occurs after the kidney is exposed to contrast for 30-60 minutes. There is a belief that (a) prolonged exposure to contrast or (b) exposure to higher concentration of contrast exacerbates the damage to the kidneys. Reduction of renal injury by hydration of the patient supports the hypothesis that decreasing concentration of contrast in blood that reaches the kidney is beneficial. There is also proven increased risk of renal injury in cases where a larger amount of contrast was used. There is abundant clinical evidence that hydration of patients (infusion of up to 2 liters of fluid before, during and after the procedure) reduces the effect of contrast on renal function. This evidence suggests that by increasing the distribution volume and reducing the concentration of contrast in blood plasma damage to kidneys can be moderated. Also, hydration affects intrarenal hemodynamics and decreases proximal reabsorption.

Clinical Risks and Usability

The main clinical concern associated with a blood fluid replacement therapy such as hemofiltration will be associated with the electrolyte composition of blood and clearance of substances with small molecular weight such as drugs.

Usability issues are concentrated around the need to maintain the supply of sterile replacement fluid (normally supplied in large 6-liter bags) connecting bags to the machine every 40 minutes and the disposal of effluent. For reference, standard bottled water fountain bottle is 19 liters. Storing and moving around this amount of volume is not a trivial task.

Limitations of Hemofiltration and Dialysis

All of the devices described prior to this point are customized general-purpose high rate "net zero" hemofiltration machines or dialysis machines. They could be used to filter out small solutes from blood for as long as it is not protein bound and is distributed in a reasonable volume. They share several common weaknesses when applied to the task of removing radiocontrast.

1. They can reduce the cumulative renal load of contrast by as much as 50% but can not eliminate it
2. They can only slightly reduce the exposure of kidneys to the initial dose of highly concentrated contrast in blood
3. They require handling, disposal and storage of large volumes of fluids
4. They require high extracorporeal blood flow that implies higher inherent risk of blood loss, larger priming volume, bigger pumps and other components
5. They could be associated with electrolyte imbalance
6. They can clear some amount of small and medium molecular weight solutes from blood

SUMMARY OF THE INVENTION

Cardiac Catheterizations

An alternative solution was proposed that eliminates all of the above shortcomings but introduces some new limitations. The majority of procedures performed under fluoroscopic guidance are cardiac procedures. Table below lists the approximate number of cardiac catheterization procedures per year. All of these procedures require contrast use. Therapeutic procedures require more contrast than diagnostic ones.

| Procedure Type | Procedures per year |
| --- | --- |
| Coronary stenting | 750,000 |
| PTCA without stenting | 250,000 |
| Diagnostic | 1,500,000 |
| Total procedures | 2,500,000 |

The cardiac vascular anatomy offers a unique solution to the contrast removal problem. About 80% of coronary blood flow (almost all of the left ventricle blood supply but little of the right coronary blood flow) drains into the coronary sinus. The coronary sinus is a relatively large appendage that opens into the right atrium of the heart. Since coronary contrast injections are most commonly directed into either the left ascending coronary artery (LAD), or left circumflex artery, the entire bolus of contrast, e.g., 1 to 2 ml of contrast, reemerges in the coronary sinus as a 20 ml bolus of blood and the contrast bolus almost undiluted by blood. In order to be certain that all of the contrast has been captured a 30 to 60 ml volume will be entrained. The coronary sinus blood flow in an average person is about 200 ml/min. The coronary sinus empties into the right atrium of the heart (RA) where the contrast bolus is mixed into the stream of venous blood (4,000 ml/min) returning from the peripheral arterial circulation and the brain via vena cava.

A 7 or 8 F catheter with an occluding balloon is used to cannulate the Coronary Sinus (CS). Both femoral (from below) and jugular (from the top) vein approaches are possible. The catheter is connected to the extracorporeal blood circulation system. Blood is continuously pumped by the system that phasically tracks the coronary sinus flow of approximately 200 ml/min in an adult subject. Natural CS blood flow pulsates with the cardiac cycle. It is high during heart diastole and low during systole.

The blood pump is controlled continuously based on the withdrawal blood pressure feedback to maintain CS pressure within physiologic limits and the infusion pressure based upon allowable maximum infusion pressure occlusion limits which are a function of blood flow. Excessively high CS pressure can impede coronary blood flow leading to angina/ischemia. Excessively low CS pressure can cause CS to collapse around the catheter.

Pump blood flow is initiated prior to balloon inflation and CS occlusion. No filtration takes place (e.g., the ultrafiltrate pump is stopped) until the contrast is injected. Blood is reinfused into a suitable peripheral vein. Alternatively a double lumen catheter can be used to infuse blood into the vena cava or right atrium. For a 100 cm long catheter a 2.0 mm ID lumen is required to maintain withdrawal pressure less than 350 mmHg. Shorter jugular) catheter could have a 1.5 mm ID lumen.

After the inflation of the balloon the blood pump controller "takes over" the coronary venous drainage circulation. Blood flow is limited based upon withdrawal and infusion pressures. The blood is pumped through the contrast removal device but no filtration takes place until needed. It is difficult to locate a balloon catheter in the coronary sinus and inflating and deflating the balloon will lead to an increased probability of dislodgment and require greater attention and time by the interventionalist who would have to ensure that the balloon had been correctly positioned each time after inflation. Designing a system that uses continuous blood flow has a number of advantages:

1. The contrast removal system can run independent of the interventionalist and allow the physician to devote their attention to the coronary procedure;
2. Elimination of the requirement to inflate and deflate the CS balloon catheter and the checking of its location which may require the use of contrast.
3. Ability to match the physiological CS blood flow. If the blood flow extracted from the coronary sinus is not well matched with the patients physiological CS blood flow then collateral blood flow loss will occur which will result in loss of contrast.

Once contrast has been detected by the contrast sensor, predilution and ultrafiltration are initiated. The CS catheter can be made with a low pressure balloon that is not fully occluding when fully inflated. Since the coronary drainage system generates vacuum, it will suck the walls of the CS in contact with the occlusion balloon and seal the coronary sinus much better than common cannulas for CS retroperfusion uses in cardiac surgery. This method is a safety feature. If the blood pump stops for any reason, the vacuum is no longer present, the CS walls move away and CS blood will flow around the balloon into the RA. Alternatively, an external seal to CS sealing balloon can be used that does not penetrate and distend coronary sinus. The seal will suck to the ostium of the coronary sinus that is funnel shaped. For as long as there is blood flow extraction from the CS such a design can be expected to seal fairly well. Small leaks can be well tolerated by the system since only small amounts of contrast will leak out. CHF Solutions, Inc. successfully tested the concept of such a seal as part of the renal perfusion (DRT—direct renal therapy) system development.

After the initiation of predilution and ultrafiltration the blood pump flow may be reduced to increase the effect of dilution while the bolus of blood with contrast is pumped through the filter. Ischemia will not result if the CS is blocked for 1 to 2 minutes, because there is enough collateral blood flow to prevent ischemia. During this period of contrast removal, the device would alert the interventionalist that further boluses of contrast should not be delivered. Slowing the blood flow through the filter to 20 ml/min in a 60 ml volume filter will result in a contrast dilution time constant of 18 seconds assuming the replacement solution and ultrafiltrate flows are at 200 ml/min.

A more advanced architecture of a CS contrast removal system uses of two blood pumps to trap, isolate and remove ultrafiltrate with high concentration of contrast from blood while maintaining continuous blood flow through the coronary sinus at physiological blood flow. Two of the pumps are used to withdraw blood from the CS, while the other two pumps are used for the removal of ultrafiltrate and the infusion of replacement solution fluid.

After an injection (1 to 2 ml of contrast), contrast diluted with blood (10-20 ml bolus) enters the CS catheter and starts traveling towards the first of two prefilter blood pumps. The longer the duration of the injection the larger the bolus of blood entrainment required. For instance is contrast was injected over a 10 second period and the CS blood flow was 200 ml/min contrast would have been entrained into an additional volume of blood equating to 33 ml. If the injection of contrast lasts 10 seconds the full bolus to be entrained will require 20 ml+33 ml=53 ml bolus of blood. Full entrainment can be achieved with the contrast detection sensor. CS blood flow will be directed into the filter as long as the bolus of contrast is being detected. Since both blood and contrast are liquids with high viscosity, flow in the tubing is laminar. Thus, there is minimal mixing in addition to the blood that drained into CS via collaterals. Two blood pumps are used in this architecture. One blood pump is used as a bypass blood pump to keep coronary sinus blood flow at a physiological level when the prefilter blood pump is slowed to allow dilution of the bolus of contrast entrained within the filter.

Before contrast is detected the bypass blood pump is operating at a lower blood flow rate at 20% of the overall CS blood flow. Once contrast has been detected, the bypass blood pump is stopped and the bolus of diluted contrast from the CS is allowed to enter the filter. The filter has a volume of 63 ml. Once the bolus has been entrained into the filter, the prefilter blood pump is stopped or reduced and the bypass blood pump is set to the difference between the original CS blood flow and the current filter blood flow. This ensures that the CS has continuous blood flow and that deflation of the CS balloon is unnecessary. During this contrast dilution time period, the replacement solution pump and the ultrafiltrate pump are turned on and allowed to dilute the bolus of contrast within the filter. At the same time the contrast removal system visually and audibly indicates to the interventionalists that further contrast injections should not be initiated until the current bolus of contrast has been diluted. For instance an orange light could be used to indicate that the device was in the process of removing contrast and a green light could be used to indicate that the device was ready for a contrast injection.

If a further bolus of contrast were detected, the bypass pump could be stopped so as to minimize the amount of contrast returned to the patient undiluted. The device would issue an alarm indicating the presence of the bolus of contrast and would wait to complete the current contrast bolus dilution before entraining a second bolus. Once the second bolus has been entrained into the filter, the bypass pump would be reinitiated and the audible and visual indicator that a contrast bolus should not be initiated would be reestablished. After a predetermined period of dilution time the bypass pump will be returned to its partial CS blood flow and the prefilter blood pump flow would be reinitiated. Both the bypass blood pump and prefilter blood pump are controlled as a single blood pump. The ratio of bypass pump flow to prefilter blood pump flow is set based upon which action the device has to take: 1) waiting for contrast detection, 2) dilution of contrast or 3) detection of contrast when the bypass blood pump is momentarily stopped until the bolus of contrast is pumped into the filter.

It is undesirable to stop the CS blood flow during the injection of contrast because collateral veins which bypass the CS will increase in blood flow and result in the loss of contrast agent into the patients blood stream and passing through the patients kidney. The CS blood flow should be matched as closely as possible to ensure that collateral blood flow loss is minimized. Before the contrast is injected, the maximum CS blood flow is determined. Each individual is different and patients requiring angiograms may already have compromised CS blood flow. Two strategies for determining maximum CS blood flow are proposed:
1. Measure maximum blood flow directly
2. Use an algorithm based upon the resistance of the CS catheter to limit blood flow when the resistance of the CS begins to increase. This strategy has been demonstrated to work in vivo using a porcine model.

Since the coronary artery and vein have compliance (a reservoir) it is important that enough time is given to ensure that the blood flow being achieved is not due to this stored capacitance of blood and is truly the maximum CS blood flow. A stepped blood flow from 100 ml/min to 300 ml/min is initiated in increments of 25 ml/min to 50 ml/min for a period of 30 seconds after the CS balloon has been inflated. Once the maximum blood flow has been established the device sets the operational maximum blood flow to between 80 and 100% of the established maximum blood flow.

Contrast detection may be achieved extracorporeally by one of three methods: 1) conductivity/capacitance, 2) Hct, and 3) radio opacity. Testing has also demonstrated that the conductivity of contrast is higher than blood and that the use of a conductivity sensor or capacitive sensor will adequately detect the presence of contrast even at 1 to 2% concentration in blood. The use of a Hct sensor is also possible because the dilution of blood with contrast reduces the Hct. A Hct sensor may be used to detect that blood has been diluted. It is well recognized that the purpose of a contrast agent is to become visible under x-ray so the detection of contrast is possible via a sensor detection mechanism that uses the attenuation of an x-ray signal via the presence of the contrast agent in blood. The sensor and detector would be placed across on either side of the patient circuit tubing. Blood and saline would not attenuate the signal sufficiently to cause detection but the presence of contrast would. Acoustic methods were also tried but it was found that the effect of the increased bulk modulus counteracted the increase in density and made it impossible to accurately detect the presence of contrast even at high concentration levels.

In a first embodiment, the invention is a method to remove a contrast agent injected into the blood of a patient using an extracorporeal circuit having at least a withdrawal conduit, a filter, an infusion conduit and a filter by-pass conduit, wherein said method comprises: positioning a withdrawal catheter into or proximate to a chamber of the heart of the patient; withdrawing blood from the chamber into the withdrawal catheter and to a withdrawal conduit of the extracorporeal circuit; routing blood from the withdrawal conduit through the by-pass conduit and to the infusion conduit which infuses the blood into the patient, and detecting the contrast agent in the blood flow through the extracorporeal blood circuit and thereafter routing substantially all of the blood from the withdrawal conduit through the filter and to the infusion conduit which infuses the filtered blood into the patient, wherein the filter substantially removes the contrast agent from the withdrawn blood.

In a second embodiment, the invention is a method to remove a contrast agent injected into the blood of a patient using an extracorporeal blood circuit having at least one withdrawal pump, a filter and a controller, wherein said method comprises: inserting a withdrawal catheter into or proximate to a chamber of the heart of the patient; withdrawing blood from the chamber into the withdrawal catheter; detecting the contrast agent in the blood flow through the extracorporeal blood circuit, inhibiting an injection of additional contrast agent into the blood while the contrast agent is being detected; filtering the contrast agent from the blood through the filter, and infusing filtered blood into the patient.

In a third embodiment, the invention is a method to assist in the removal of a contrast agent injected into the blood of a patient using an extracorporeal blood circuit having at least one withdrawal pump, a filter and a controller, wherein said method comprises: inserting a withdrawal catheter in or proximate to a chamber of the heart of the patient; withdrawing blood from the chamber into the withdrawal catheter; passing the withdrawn blood through the blood circuit; filtering the contrast agent from the blood through the filter; infusing filtered blood into the patient, and automatically regulating a rate of withdrawal of the blood from the chamber based on a withdrawal pressure and a desired withdrawal pressure as determined by the controller.

In a fourth embodiment the invention is an extracorporeal blood circuit comprising: a withdrawal conduit connectable to a coronary withdrawal catheter; a withdrawal pump connectable to the withdrawal conduit, wherein a pumping rate of the withdrawal pump determines a blood withdrawal rate from the coronary withdrawal catheter; a filter having an input connected to the withdrawal conduit and a blood output connected to an infusion conduit and a filtrate output connected to a filtrate conduit; a filtrate measurement device to determine an amount of filtrate removed from the blood in the filter; a fluid supplementation conduit providing a blood replacement fluid to at least one of the withdrawal conduit, filter and infusion conduit; a supplementation pump connectable to the fluid supplementation conduit, wherein a pumping rate of the supplementation pump determines a rate at which the blood replacement fluid flows into the blood flowing through the blood circuit, and a controller regulating the pumping rate of the supplementation pump such that the rate of the blood replacement fluid provides an amount of blood replacement fluid to the at least one of the withdrawal conduit, filter and infusion conduit so as to substantially match the amount of filtrate removed.

In a fifth embodiment the invention is an extracorporeal blood circuit comprising: a withdrawal conduit connectable to a coronary withdrawal catheter; a withdrawal pump connectable to the withdrawal conduit, wherein a pumping rate of the withdrawal pump determines a blood withdrawal rate from the coronary withdrawal catheter; a filter having an input connected to the withdrawal conduit and a blood output connected to an infusion conduit and a filtrate output connected to a filtrate conduit; a by-pass conduit coupled to the withdrawal conduit at a position upstream of the filter and said by-pass conduit also coupled to the infusion conduit, wherein a by-pass pump connectable to the by-pass conduit determines a blood flow rate through the by-pass conduit, and a controller regulating the pumping rate of the by-pass pump such the blood flow rate through the by-pass conduit is substantially zero while a contrast agent is in the blood.

In a sixth embodiment the invention is an extracorporeal blood circuit comprising: a withdrawal conduit connectable to a coronary withdrawal catheter; a withdrawal pump connectable to the withdrawal conduit, wherein a pumping rate of the withdrawal pump determines a blood withdrawal rate from the coronary withdrawal catheter; a filter having an input connected to the withdrawal conduit and a blood output connected to a filtered blood reservoir and a filtrate output connected to a filtrate conduit; a by-pass conduit coupled to the withdrawal conduit at a position upstream of the filter and said by-pass conduit also coupled to the infusion conduit, wherein a by-pass pump connectable to the by-pass conduit determines a blood flow rate through the by-pass conduit, and a controller regulating a pumping rate of the by-pass pump such the blood flow rate through the by-pass conduit is substantially zero while a contrast agent is in the blood and wherein said controller regulates a pumping rate of the withdrawal pump to draw blood with contrast agent through the filter and to subsequently reverse the flow of blood through the filter to draw filtered blood from the reservoir and into the by-pass conduit.

In a seventh embodiment the invention is a method for removing a contrast agent using an extracorporeal blood circuit having a blood withdrawal pump, a by-pass pump, and a filter, said method comprising: withdrawing blood from a coronary withdrawal catheter positioned to draw substantially all blood flowing from a chamber of a heart of a patient such that the withdrawn blood flows into a withdrawal conduit; infusing the withdrawn blood into the patient via a by-pass conduit and infusion conduit without treating the blood; injecting a contrast agent into a blood vessel of the patient such that the contrast agent flows with blood into the chamber of the heart; after injecting the contrast agent, substantially ceasing blood flow through the by-pass conduit and directing the blood flow through the filter, wherein the filter extracts the contrast agent from the blood, and infusing filtered blood into the patient.

DESCRIPTION OF PREFERRED EMBODIMENT

Figure 1:
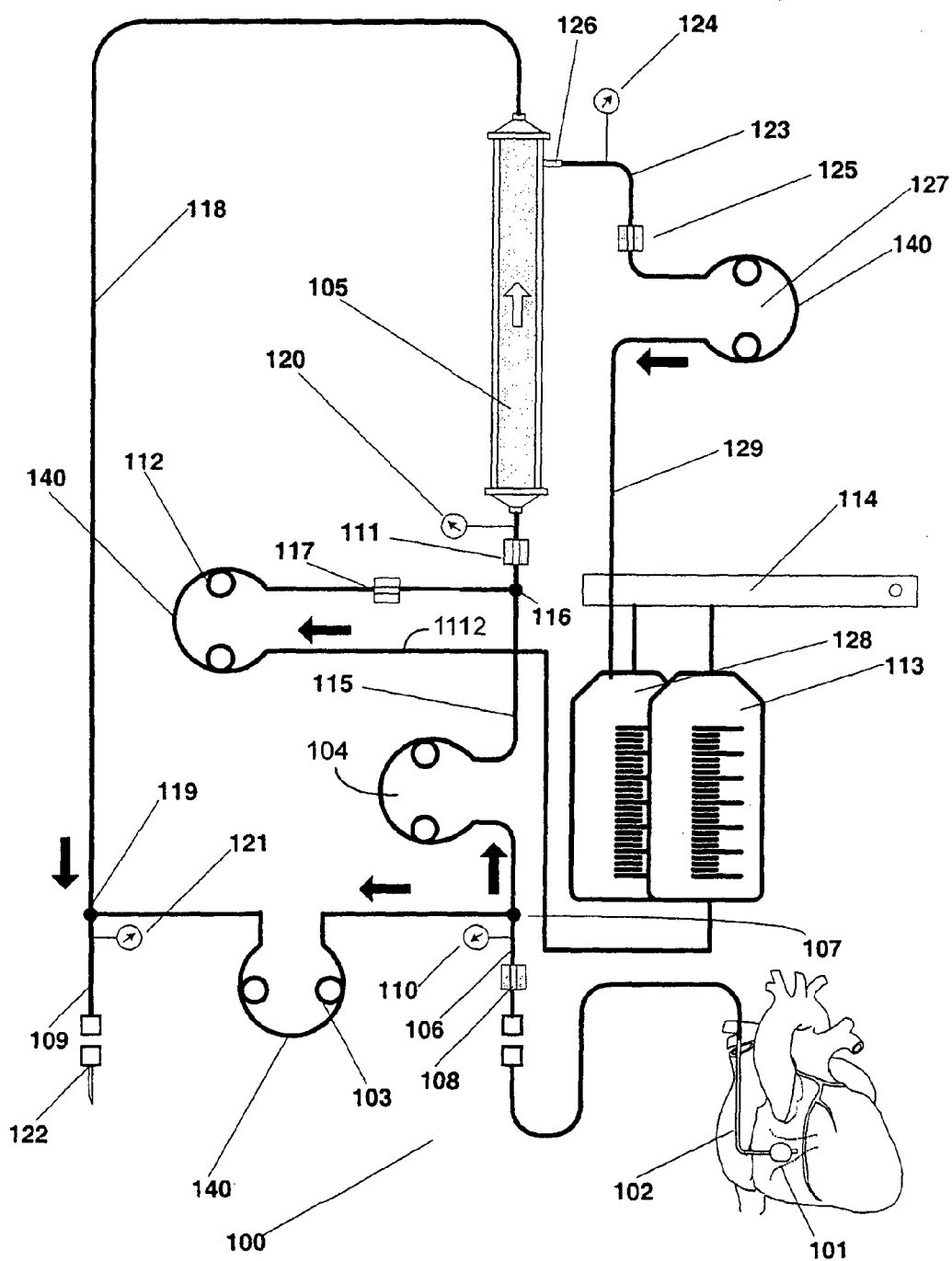
FIG. 1 is a schematic diagram of a contrast removal device with an ultrafiltrate pump.

A method and device is disclosed for the removal of radio-contrast media from blood. There is a long-felt need for a device to automatically remove contrast from a patient before the kidneys are exposed to contrast agent resulting in contrast nephropathy. A novel blood withdrawal and infusion system has been developed that enables rapid recovery of contrast while maintaining coronary sinus (CS) blood flow. Control algorithms are described that provide safe recovery from occlusions in the CS, without participation of an operator, loss of circuits to clotting, or annoying alarms.

A controller and device have been developed:

1. That compensates for and remedies temporary CS collapse during blood or occlusions difficulties in the withdrawal or infusion lines. Not all episodes of a vein collapse require intervention from a doctor or nurse, and do not require that blood withdrawal ceased for an extended period. For example, vein collapse can temporarily occur during a venous spasm or temporary reduction in CS blood flow, causing the vein to collapse in a manner that is too rapid to anticipate and temporary. There has been a need for such a control system for an extracorporeal circuit that can automatically recover from such temporary occlusions. The controller may also temporarily stop blood withdrawal when such a vein collapse occurs and, in certain circumstances, infuses blood into the collapsed vein to reopen the collapsed vein.

2. That uses a bypass pump to ensure continued withdrawal of CS blood flow extracorporeally during contrast removal. Moreover, the controller also prompts the operator to halt contrast injections during the process of contrast removal.

3. That uses a controller to exactly match the fluid replacement rate with the fluid extraction rate to minimize errors in fluid loss and gain due to inaccuracies in the peristaltic pump flow control. Peristaltic pumps are generally accurate to approximately 10% of flow setting. This inaccuracy results due to manufacturing variations in tubing diameter and variances in the elastic recoil of the tubing due to negative pressures, material properties and degeneration of the tubing elastic properties over time. For instance if the cross-sectional diameter of the tubing does not recoil to the expected circle shape every time and is better represented as an oval then the flow rate will not be exact and consistent either.

4. That uses the measured TMP (Trans Membrane Pressure) of the filter as feedback to adjust the rate of replacement solution to ensure the filter is not exposed to excessively high pressures. This algorithm prevents annoying alarms due to filter fouling and maintains safe operation of the device while continuing therapy. Stopping treatment and replacing the filter is highly intrusive and would create a major disruption to the interventional procedure.

In response to occlusions blood both the bypass blood pump and prefilter blood pumps are reduced automatically using pressure as feedback. If occlusion is removed, these flow rates are restored immediately and automatically. The operator is alarmed if occlusions are prolonged or frequent. An alarm is canceled automatically if the occlusion is alleviated, and blood flows are restored. Myocardial blood supply is from the right and left coronary arteries, which run over the surface of the heart giving branches to the endocardium (the inner layer of the myocardium). Venous drainage is mostly via the coronary sinus into the right atrium, but a small proportion of blood flows directly into the ventricles through the Thebesian veins, delivering unoxygenated blood to the systemic circulation. Oxygen extraction by the tissues is dependent on consumption and delivery. Myocardial oxygen consumption is higher than in skeletal muscle (65% of arterial oxygen is extracted as compared to 25%). Therefore any increased myocardial metabolic demand must be matched by increased coronary blood flow. This is a local response, mediated by changes in coronary arterial tone, with only a small input from the autonomic nervous system. Thus it is important that CS blood flow be maintained during contrasts removal to prevent ischemia from occurring to the heart muscle.

The exemplary apparatus described here is a contrast removal device designed for the extraction of plasma water and contrast from human blood. To extract plasma water and contrast the apparatus includes a filter. The filter has a membrane that is permeable to water and small molecules and impermeable to red blood cells, proteins and other large solute particles. The filter is permeable to particles of less than 40,000 to 60,000 daltons.

Blood is withdrawn via two blood pumps the prefilter blood pump and the bypass blood pump. The prefilter blood pump only operates when a contrast bolus has been detected. Otherwise the bypass blood pump maintains physiological blood flow from the coronary sinus preventing the need for deflation and re-inflation of the balloon catheter. When contrast is detected blood the bypass blood pump is stopped to prevent contrast from leaking back into the patients circulatory system via the bypass pump and CS blood flow is maintained at its physiological blood flow resulting in the heart being oblivious to the transition by the prefilter blood pump.

FIG. 1 illustrates the operation and fluid paths of blood, ultrafiltrate and replacement solution fluid through the blood circuit of the contrast removal system. Blood is withdrawn from the patient through the CS 101 with a balloon catheter 102 or other occlusive type catheter via the femoral or IJ (internal Jugular). The blood flow from the CS into the withdrawal tubing is dependent upon the fluid pressure in that tubing which is controlled by the blood pumps 103 and 104. The blood pump 103 is a bypass pump which redirects blood flow from the filter maintaining CS blood flow during the contrast removal. The blood pump 104 is a withdrawal and filter pump and it withdraws blood and directs the withdrawn blood to the filter 105.

The length of the withdrawal tubing 106 between the balloon catheter 102 and the blood pump wye 107 is approximately 2 meters. The withdrawal tubing may be 3.5 mm ID tubing. At 200 ml/min blood flow it will generate acceptable hydraulic resistance in the order of 60 mmHg. In 5 seconds (assuming 2.0 meter length), after exiting the catheter and entering the blood tubing, the bolus of contrast will reach the contrast sensor 108 located before the blood pumps 103 and 104. If a lower resistance of tubing is desired, standard 4.5 mm ID dialysis tubing can be used. In 9 seconds (assuming 2.0 meter length), after exiting the catheter 102 and entering the blood tubing 106, the bolus of contrast will reach the contrast sensor located before the blood pumps. With the 3.5 mm ID tubing, the volume of the two-meter patient segment is 16 ml. When no contrast is detected both the by pass blood pump 103 and the prefilter blood pump 104 are operational. The bypass blood pump is set to 20% of the total CS blood flow and the prefilter blood pump is set to 80% of the total CS blood flow.

The withdrawal pressure is monitored with an inline withdrawal pressure sensor 110. This pressure sensor is located upstream of the T-junction 107 where it can measure the withdrawal pressure for both blood pumps 103 and 104. The bypass blood pump 103 returns blood flow via the 2 meters length of infusion tubing 109. The prefilter blood pump displaces the blood from the CS catheter through the pre filter tubing segment 115 past the air detector 111 and past the pre filter pressure sensor 120 before entering the filter 105. The replacement solution pump 112 (which is also referred to as a supplementation pump) extracts dilution liquid from the bag 113 which is attached to the weight scale 114. The replacement solution pump 112 pumps liquid via a fluid supplementation conduit 1112 into the prefilter tubing segment 115 down stream of the air detector 111 at a union 116. Any air entrained by the replacement solution pump 112 will be detected by the air detector 111. A separate air detector 117 may also be placed between the replacement solution pump outlet 112 and the union 116 to prevent air from entering the blood stream in the event that the replacement solution bag 113 becomes empty. Blood exits the filter 105 via tubing segment 118 before rejoining the bypass blood pump flow at the union 119. The infusion pressure sensor 121 is located downstream of the union 119 where it is able to measure the combination of the pressure generated by the bypass blood pump and the prefilter blood pump. Blood may be returned to the patient by a number of access options: via a separate cannulae in the femoral/jugular vein; via a dual lumen infusion and withdrawal catheter or via a side port in a sheath.

At the same time that replacement solution is being infused into the prefilter blood line the ultrafiltration/fluid removal pump is also being run. Ultrafiltrate is removed when the ultrafiltration pump 127 rotates clockwise and ultrafiltrate is removed from the blood in the filter via a tubing segment 123. The ultrafiltrate extraction process is monitored for the presence of occlusions with the ultrafiltrate pressure sensor 124 and for the presence of blood leaks detected using a blood leak detector 125. Both sensors are positioned between the filter extraction port 126 and the inlet to the ultrafiltrate pump 127. The blood leak detector 125 detects the presence of a ruptured/leaking filter, or separation between the blood circuit and the ultrafiltrate circuit. In the presence of a leak, the ultrafiltrate fluid will no longer be clear and transparent because the blood cells normally rejected by the membrane will be allowed to pass. The blood leak detector detects a drop in the transmissibility of the ultrafiltrate line to infrared light in the frequency range of 820 nm and declares the presence of a blood leak. This is close to the isospectic point of blood making the sensor insensitive to the amount of oxygen attached to the hemoglobin.

The ultrafiltrate pump 127 displaces the ultrafiltrate into the ultrafiltrate bag 128 via the tubing segment 129. The ultrafiltrate bag 128 is measured with the same weight scale 114 used to measure the weight of the replacement solution 113. Thus since the replacement solution pump and ultrafiltrate pump are supposed to match in flow the weight measured by the weight scale 114 should not change during operation otherwise there is a mismatch between flow rates. A weight scale controller is used to ensure that the flow rates match by adjustment of the replacement solution pump within prearranged adjustment limits to ensure that the weight scale continues to measure the set weight measured at the start of treatment.

Figure 2:
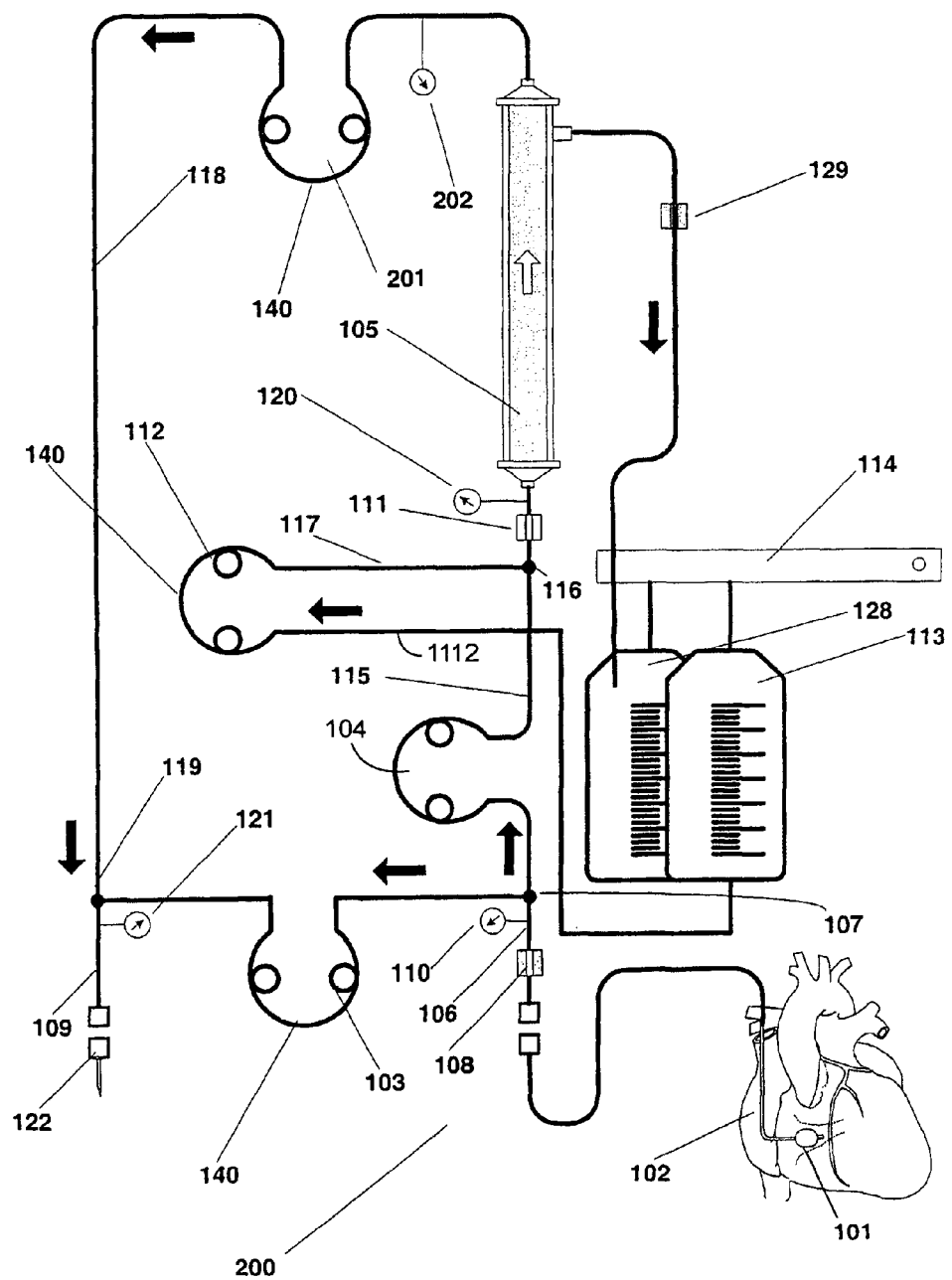
FIG. 2 is a schematic diagram of a contrast removal device with a post filter blood pump.

FIG. 2 shows a second embodiment that is a slight modification to FIG. 1. In this design the ultrafiltrate pump 127 has been removed and replaced with a post filter blood pump 201. Ultrafiltration is achieved by creating a difference in blood flow between prefilter blood pump and post filter blood pump. This variation is provided to show that variations of pump configurations are possible and are within the scope of this invention. A post filter pressure transducer 202 may also be placed at the outlet of the filter 105 to measure post filter pressure.

Figure 16:
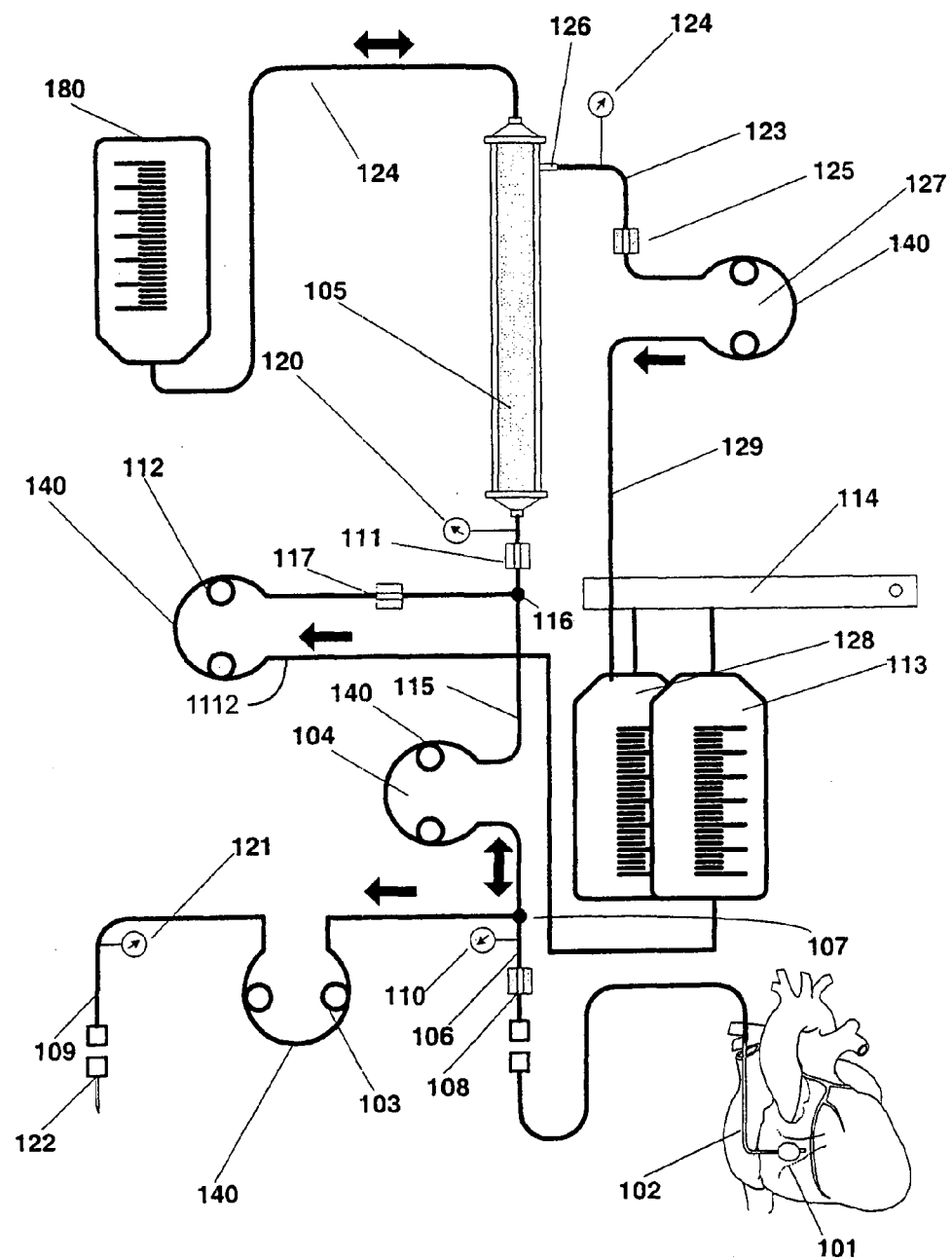
FIG. 16 is a schematic diagram of a contrast removal device which operates in a batch mode.

FIG. 16 shows a third embodiment in which the contrast removal from the blood using the filter 105 is performed in a batch process. The blood is first withdrawn and collected in a bag 180. It may also be filtered during this process but since the blood flow will be as high as 200 ml/min the infusion duration for blood into the filter and collection bag will be as short as 6 to 12 seconds (20 to 40 ml). The entrained blood (which contains of contrast) later pumped back through the filter by the reversal of the prefilter blood pump and is infused into the patient after contrast is removed. Blood is pumped into the blood collection bag post filter until the bolus of contrast has been entrained plus an additional 20 ml of non contrast diluted blood to ensure that the contrast is entrained within the filter and bag only. The prefilter blood pump is stopped and the bypass blood pump is restarted switching the control of the CS physiological blood flow from the prefilter blood pump to the bypass blood pump. The replacement solution pump and the ultrafiltrate pump are started and the blood from the in the blood bag is cleaned and returned to the patient via the reversal of the prefilter blood pump and bypass blood pump. During the prefilter blood pump reversals the bypass blood pump and the prefilter blood pump are controlled as a single blood pump to maintain CS blood flow. The bypass blood pump flow is increased by the reversal rate of the prefilter blood pump flow to account for the additional flow generated by the additional flow generated by the reversal of the prefilter blood pump. Thus if the CS was totally occluded the bypass blood pump would match the prefilter blood pump exactly ensuring the withdrawal pressure would be controlled to 0 mmHg. Blood from the blood bag may be returned in batches of filter blood volumes or at a continuous rate if adequate dilution can be ensured. The advantage of such a system is that the contrast bolus entrainment is no longer dependent upon filter blood volume and if multiple contrast injections were injected sequentially, capture can always be ensured as long as the capacity of the blood bag volume is sufficient. With such a scheme for the removal of contrast it will necessary to ensure that the patients blood volume is not depleted by more than 300 ml (the average volume of a blood donation) otherwise hypovolemia may ensure.

FIG. 16 illustrates the operation and fluid paths of blood, ultrafiltrate and replacement solution fluid through the blood circuit of the contrast removal system. Blood is withdrawn from the patient through the CS 101 with a balloon catheter 102 or other occlusive type catheter via the femoral or IJ (internal Jugular). The blood flow from the CS into the withdrawal tubing is dependent upon the fluid pressure in that tubing which is controlled by the blood pumps 103 and 104. The blood pump 103 is a bypass pump which redirects blood flow from the filter 105 maintaining CS blood flow during the contrast removal. The blood pump 104 is a filter pump and it directs blood flow to the filter 105 and blood collection bag 180 when contrast has been detected. When no contrast is detected the bypass blood pump 103 may be the only pump operational. The prefilter blood pump 104 may be returning blood which has had contrast removed or may be stopped. The bypass blood pump is set to 100% of the total CS blood flow when blood containing contrast has not been detected or is not in the process of removal otherwise it is set to 0 ml/min. The prefilter blood pump is set to 100% of the total CS blood flow when contrast has been detected and the bypass blood pump is set to 0 ml/min to prevent contrast being returned to the patient. The withdrawal pressure is monitored with an inline withdrawal pressure sensor 110. This pressure sensor is located upstream of the wye where it can measure the withdrawal pressure for both blood pumps 103 and 104. The bypass blood pump 103 returns blood flow via the 2 meters length of infusion tubing 109. The prefilter blood pump displaces the blood from the CS catheter through the prefilter tubing segment 115 past the air detector 111 and past the prefilter pressure sensor 120 before entering the filter 105 and passing into the blood collection bag 180. The replacement solution pump 112 extracts replacement solution from the bag 113 which is attached to the weight scale 114. The replacement solution pump 112 pumps replacement solution into the prefilter tubing segment 115 down stream of the air detector 111 at a union 116. Any air entrained by the replacement solution pump 112 will be detected by the air detector 111. A separate air detector 117 may also be placed between the replacement solution pump outlet 112 and the union 116 to prevent air from entering the blood stream in the event that the replacement solution bag 113 becomes empty. Blood exits the filter 105 via tubing segment 118 entering the blood collection bag 180. The infusion pressure sensor 121 is located at the exit of the bypass blood pump 103 where it is able to measure the pressure generated by the bypass blood pump returning blood through the infusion cannulae 122.

Blood may be returned to the patient by a number of access options: via a separate cannulae in the femoral/jugular vein; via a dual lumen infusion and withdrawal catheter or via a side port in a sheath. At the same time that replacement solution is being infused=the ultrafiltration/fluid removal pump is also extracting ultrafiltrate. Ultrafiltrate is removed when the ultrafiltration pump 127 rotates clockwise and ultrafiltrate is removed from the blood in the filter via a tubing segment 123. The ultrafiltrate extraction process is monitored for the presence of occlusions with the ultrafiltrate pressure sensor 124 and for the presence of blood leaks detected using a blood leak detector 125. Both sensors are positioned between the filter extraction port 126 and the inlet to the ultrafiltrate pump 127. The blood leak detector 125 detects the presence of a ruptured/leaking filter, or separation between the blood circuit and the ultrafiltrate circuit. In the presence of a leak, the ultrafiltrate fluid will no longer be clear and transparent because the blood cells normally rejected by the membrane will be allowed to pass. The blood leak detector detects a drop in the transmissibility of the ultrafiltrate line to infrared light in the frequency range of 820 nm and declares the presence of a blood leak. This is close to the isospectic point of blood making the sensor insensitive to the amount of oxygen attached to the hemoglobin.

Contrast removal via dilution may occur once the prefilter blood pump 104 is starts to entrain contrast. Once the bolus has been entrained in the filter and 105 and the blood collection bag 180 the prefilter blood pump may be stopped and the bypass blood pump restarted at the previous blood flow for the prefilter blood pump. Both pumps use the withdrawal pressure sensor 110 to ensure CS physiological blood flow. Assuming that a 40 ml blood volume filter was used the ultrafiltrate pump flow rate and replacement solution pump flow rate would be set to 100 ml/min. To remove 95% of the contrast contained within the filter (20 ml/100 ml/min)*3=36 seconds would be required to dilute the contrast. After the bolus of blood within the filter has been diluted, the 20 ml volume of blood entrained within the filter could be returned to the patient by speeding up the bypass blood pump by the rate at which the prefilter blood pump was set to. After displacing 20 ml the prefilter blood pump would be stopped and the dilution process would be restarted until the volume of blood entrained within the filter and blood collection bag has been returned. This system has the advantage that if the operator were to give another bolus of contrast while dilution was in process the prefilter blood pump could be reversed and the bypass blood pump stopped and the bolus of contrast entrained.

The ultrafiltrate pump 127 displaces the ultrafiltrate into the ultrafiltrate bag 128 via the tubing segment 129. The ultrafiltrate bag 128 is measured with the same weight scale 114 used to measure the weight of the dilution fluid 113. Thus since the replacement solution pump and ultrafiltrate pump are supposed to match in flow the weight measured by the weight scale 114 should not change during operation otherwise there is a mismatch between flow rates. A weight scale controller is used to ensure that the flow rates match by adjustment of the replacement solution pump within prearranged adjustment limits to ensure that the weight scale continues to measure the set weight at the start of treatment.

In order to prevent the batch system from clotting once the initial bolus of blood has been entrained within the filter local anticoagulation within the circuit can be used. This would be achieved with the addition of a T port situated downstream of the T junction 107 for the purpose of infusion heparin or citrate. This can be achieved with an standard IV infusion pump. Since the period between contrast injections may vary from seconds to minutes infusing replacement solution into the filter after the blood has been returned to the patient will increase filter life. The size of the bolus will be dependent upon the volume of the filter and tubing between the filter and the blood collection bag. Assuming a filter with a 20 ml volume were used 40 ml of replacement solution could be infused into the filter after the completion of the reversal of the blood pump. This additional volume can be measured accurately by the decrease in weight of the weight scale and can be extracted from the next bolus of blood infused into the blood collection bag and filter during the subsequent dilution of the blood entrained within the filter. Since blood and contrast solutions will be entrained into the filter based upon its volume capacity for dilution it will be necessary to work out how much extra ultrafiltrate to remove to ensure a net loss of zero for the replacement solution. For example if 30 ml of blood are entrained on top of the 40 ml of replacement solution this means that there are now 70 ml entrained between the filter and blood collection bag. During ultrafiltration this additional 40 ml volume may be recovered by increasing the ultrafiltrate rate to account for the loss so the net loss over treatments is 0 ml.

Figure 3:
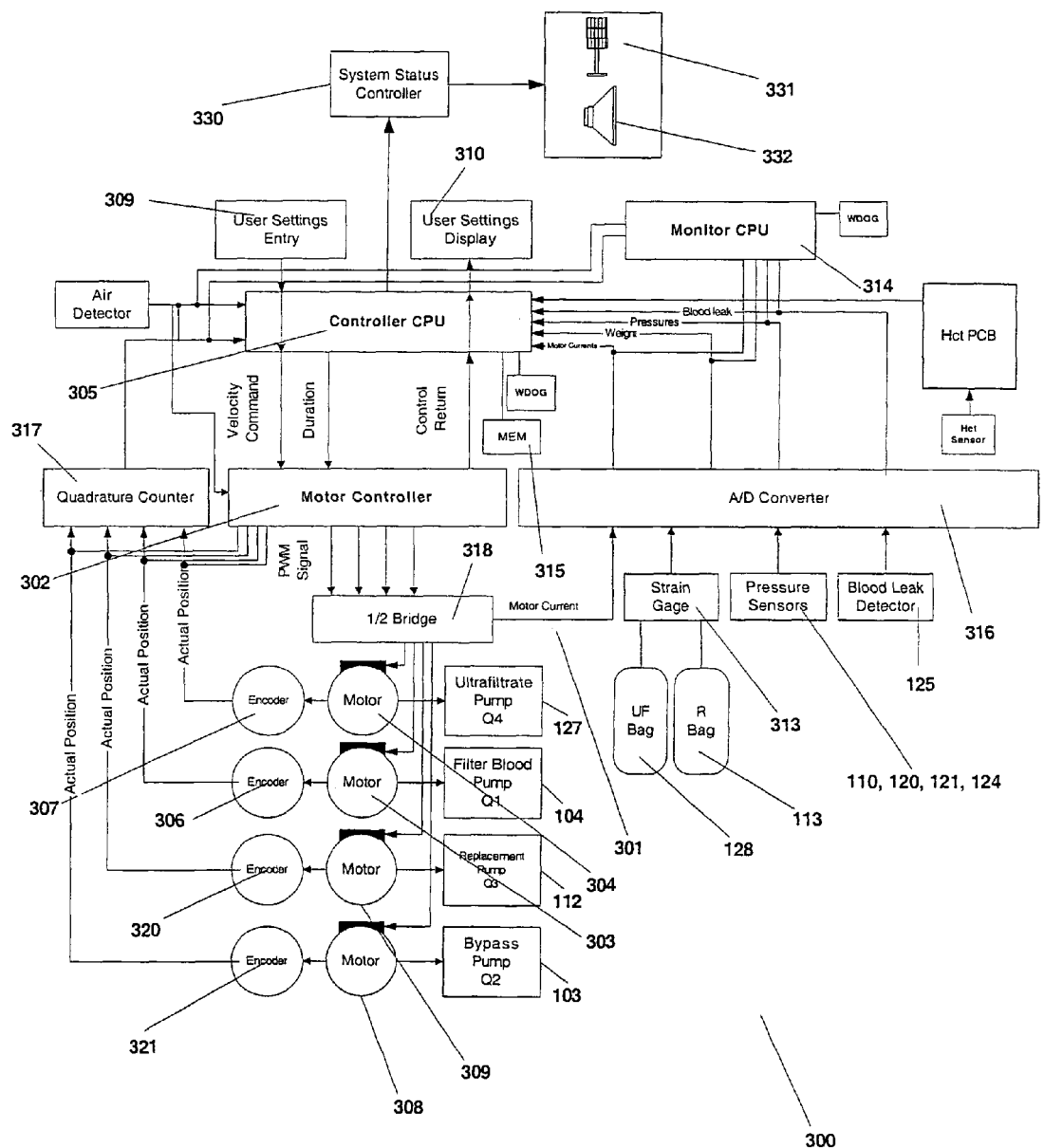
FIG. 3 shows the electronic architecture of the contrast removal device.

FIG. 3 illustrates the electrical architecture of the contrast removal system 300 showing the various signal inputs and actuator outputs to the contrast removal system. The user-operator inputs the mode of operation into the controller by pressing buttons on a membrane interface keypad 309 on the controller. The device has four main modes or states of operation, Stop Mode, Prime Mode, Manual Mode and Run Mode. Stop mode is the default status of the device and all pump rotations are ceased. Prime Mode is used to prime the circuit before extracorporeal connections are made to the circuit. The device automatically primes the circuit with saline eliminating air bubbles and flushing the circuit prior to use. Manual Mode allows the operator to advance specific pumps to eliminate air bubbles without having to hand crank pumps in the event of an air ingress. Run Mode is the operational mode of the device where contrast removal is enabled. These settings may include the maximum flow rate of blood through the system, maximum time for running the circuit to filter the blood, the maximum ultrafiltrate rate and the maximum ultrafiltrate volume. The settings input by the user are stored in a memory 315 (mem.), and read and displayed by the controller CPU 305 (central processing unit, e.g., microprocessor or micro-controller) on the display 310.

The controller CPU regulates the pump speeds by commanding a motor controller 302 to set the rotational speed of the prefilter blood pump 104, ultrafiltrate pump 127, replacement solution pump 112, and bypass blood pump 103 to a certain speed specified by the controller CPU 305. Feedback signals from the pressure transducers sensors 120, 121, 110 and 124 are converted from analog voltage levels to digital signals in an A/D converter 316. The digital pressure signals are provided to the controller CPU as feedback signals and compared to the intended pressure levels determined by the CPU. In addition, the digital pressure signals may be independently assessed by the monitor CPU 314 to ensure that the contrast removal device is functioning within expected operational pressure ranges.

The motor controller 302 controls the velocity, rotational speed of the pump motors 303, 304, 314 and 315. Encoders 307, 306, 320 and 321 are mounted to the rotational shaft of each of the motors to provide feedback on position via quadrature signals, e.g., a pair of identical cyclical digital signals and 90 degrees out-of-phase with one another. These signal pairs are fed to a quadrature counter within the motor controller 302, controller CPU 305 and monitor CPU 314 to give both direction and position of the motor. The direction is determined by the signal lead of the quadrature signals. The position of the motor is determined by the accumulation of pulse edges. Actual motor velocity is computed by the motor controller as the rate of change of position. The controller calculates a position trajectory that dictates where the motor must be at a given time interval and the difference between the actual position and the desired position is used as feedback by the motor controller. The motor controller then modulates the percentage of the on time of the PWM (Pulse Width Modulated) signal sent to the one-half 318 bridge circuit to minimize the error. A separate quadrature counter 317 is independently read by the Controller CPU and Monitor CPU to ensure that the Motor Controller is correctly controlling the velocity of the motor. This is achieved by differentiating the change in position of the motor over time.

The monitor CPU 314 provides a safety check that independently monitors each of the critical signals, including signals indicative of blood leaks 125, pressures in blood circuit 110, 120, 121, 124, weight of filtrate bag 313, motor currents 324, air in blood line detector 323 and motor speed/position 317. The monitor CPU has stored in its memory safety and alarm levels for various operating conditions of the contrast removal system. By comparing these allowable preset levels to the real-time operating signals, the monitoring CPU can determine whether an independent safety alarm should be issued, and has the ability to independently stop both motors and reset the motor controller and controller CPU if necessary.

The Controller CPU and Monitor CPU each have independently strobe external watch dogs which have the ability to reset the entire system bringing it to a safe state and resulting in the annunciation of an alarm if the watchdogs are not strobed at the correct frequency. Such a fail safe watchdog system is common in embedded hardware devices controlled by software.

The Controller CPU also informs the operator when contrast removal is in progress or in the event of a system alarm 332 by the audible annunciation of an alarm and the visual display of the system status 331. The visual display may consist of a green, orange and red light. A red flashing light indicates a warning and that a fault has been detected that requires immediate attention, an orange flashing light indicates an alert which is not of immediate concern but requires the attention of the operator and a solid green light indicates normal system status. In such a device a solid orange light could be used to indicate that contrast is being removed. A separate indicator or a solid orange light could be used to indicate to the operator that the device was removing contrast. A distinct audio tone cuing the interventionalist to the state of the device could also be generated obviating the need for the interventionalist to examine the device to determine its state.

Pump Design:

The peristaltic pumps used for the bypass blood pump 103, filter blood pump 104, ultrafiltrate pump 127 and replacement solution pump 112 are of similar design and consist of double roller occlusive peristaltic pumps. The peristaltic pumps are rotated by a brushless DC motor housed within the contrast removal device. Each pump includes a rotating pump head with orbiting rollers that are applied to a half-loop 140 in the circuit 100. The orbital movement of the rollers applied to tubing forces blood to move through the circuit. This half-loop segment may have the same ID as does the other blood tubing portions of the blood circuit. The speed of the pumps may be adjusted by the controller to be fully occlusive until a pressure limit of 20 psig (pounds per square inch gauge i.e. referenced to atmosphere) is reached. At pressures greater than 20 psig, the pump rollers relieve because the spring force occluding the tube will be exceeded and the pump flow rate will no longer be directly proportional to the motor velocity because the rollers will not be fully occlusive and will be relieving fluid. This safety feature ensures the pump is incapable of producing pressure that could rupture the filter.

Pressure Sensors:

The pressure sensors are of the solid state flow-through type sensor suitable for blood pressure measurements. It is preferable that the sensor have no bubble traps, separation diaphragms or other features included in the sensor that might cause stagnant blood flow and lead to inaccuracies and delays in the pressure measurement. The pressure sensors are designed to measure negative (suction) pressure down to −400 mm Hg and a positive pressure as high as 600 mm Hg. All pressure measurements in the contrast removal system are referenced to static head pressure offsets.

The static head pressure offsets arise because of the tubing placement and the pressure sensor height with respect to the patient connection. The pressure transducers Pw (withdrawal pressure sensor 110), Pin (infusion pressure sensor 121), the Pp (pre filter pump pressure) and Puf (filtrate pressure sensor 111) produce pressure signals that indicate a pressure relative at each sensor location. Prior to treatment, the sensors are zeroed by determining appropriate pressure offsets. These offsets are used to eliminate, i.e., "zero out", the static pressure in the blood circuit and ultrafiltrate circuit due to gravity. The offsets are determined with respect to atmospheric pressure when the blood circuit is filled with saline or blood, and the pumps are stopped. The offsets are measures of the static pressure generated by the fluid column in each section, e.g., withdrawal, return line, pre filter and filtrate tube, of the circuit. During operation of the system, the offsets measured at the start of treatment are subtracted from the raw pressure signals generated by the sensors as blood flows through the circuit. Subtracting the offsets from the raw pressure signals reduces the sensitivity of the system to static pressure heads and facilitates the accurate measurement of the pressure drops in the circuit due to circuit resistance in the presence of blood, replacement solution and ultrafiltrate flow. Absent these offsets, a false disconnect or occlusion alarm could be issued by the Controller CPU (305 in FIG. 3) because, for example, a static 30 cm column of saline/blood will produce a 22 mm Hg pressure offset.

The pressure offset for a particular sensor is a function of the fluid density "ρ", the height of the tube "h" and the earth's gravitational constant "g":

$$P\text{offset} = \rho * g * h$$

where "ρ" and "g" are constants and, thus, pressure offsets are a function of the sensor position. The pressure offsets are not experienced by the patient. Proof of this is when a tube filled with water with its top end occluded (pipette) does not allow the water to flow out. This means that the pressure at the bottom of the tube is at 0 mm Hg gage. In order to normalize the offset pressures, the offsets are measured at the start of operation when the circuit is fully primed and before the blood pump or ultrafiltrate pump are actuated. The measured offsets are subtracted from all subsequent pressure measurements. Therefore, the withdrawal pressure Pw, the infusion pressure Pin, the pump prefilter pressure Pp and the ultrafiltrate pressure Puf are calculated as follows:

$$Pw = Pw\text{Gage} - Pw\text{Offset}$$

$$Pin = Pin\text{Gage} - Pin\text{Offset}$$

$$Pp = Pp\text{gage} - Pp\text{Offset}$$

$$Puf = Puf\text{Gage} - Puf\text{Offset}$$

PwOffset, PinOffset, PpOffset and PufOffset are measured when the circuit is primed with saline, and the pumps are stopped. PwGage, PinGage and PufGage are measured in real time and are the raw, unadjusted gage pressure readings from the pressure transducers. To increase accuracy and to minimize errors due to noise, the offsets are checked for stability and have to be stable within 2 mm Hg for 1 second before an offset reading is accepted. The offset is averaged over 1 second to further reduce sensitivity to noise.

Weight Scale Design:

The weight scale 114 uses a wheatstone bridge strain gauge sensor to detect weight and has been designed to have a total weight capacity of 10 kg. Replacement solution bags are commercially available in 6 kg (maximum weights) giving the scale a suitable factor of safety. Both bags 113 and 128 are attached to the scale at the start of treatment when the Replacement solution bag is full and the ultrafiltration bag is empty. After the completion of circuit priming the target weight of the weight scale is set and remains constant for the duration of treatment unless the bags are replaced whereupon the operator informs the device of the change. A separate weight scale could also be placed between the replacement ultrafiltrate bag and the weight scale 114 to measure the weight of the ultrafiltrate bag. When the contrast bag became full the device would alarm for the condition and inform the operator to the system status. The target weight would be reset based upon reinitiating of treatment. Alternatively the volume displaced by the pumps can be integrated over time to estimate the fluid volume in the ultrafiltrate bags. Since the pumps are only 10% accurate the alarm volume has to be set to at least 10% less than the capacity of the replacement solution bag or the measured target weight at the initiation of treatment. Since contrast will be entrained in the ultrafiltrate bag during treatment some volume error will ensue. Since the specific gravity of contrast is 1.4 and the volume of contrast delivered to the patient sensitive to contrast nephropathy is expected to be less than 100 ml the maximum overall volume error that could result is less than 40 ml. 40 ml of excess replacement solution would be the net gain for the patient over the treatment. This is not considered medically significant.

Air Detector Design:

The air detector 111 uses an ultrasonic emitted and detector to detect the presence of air. Dense fluids like water are good conductors of acoustic energy whereas non dense fluids like air highly attenuate acoustic signal transmission. This property is used to detect the presence of air. When the received ultrasonic signal level drops below a preprogrammed level air detection is declared.

Filter Design:

Whole blood enters a bundle of hollow fibers from the connector on the bottom of the cap of the filter canister. There are approximately 7000 hollow fibers in the bundle, and each fiber is a filter. Blood flows through a channel approximately 0.2 mm in diameter in each fiber. The walls of the channel are porous. The pores in the wall of each channel are permeable to water and small solutes but impermeable to red blood cells, proteins and other blood components that are larger than 50,000-60,000 Daltons. Blood flow in fibers is tangential to the surface of the filter membrane. The shear rate resulting from the blood velocity is high enough such that the pores in the membrane are protected from fouling by particles, allowing the filtrate (ultrafiltrate and contrast) to permeate the fiber wall. Filtrate leaves the fiber bundle and is collected in space between the inner wall of the canister and outer walls of the fibers. The filter membrane will prevent blood cells and larger proteins from passing. Water, small molecules and radiocontrast will pass freely.

Alternatively, blood could be condensed in the filter fibers to very high hematocrit levels to maximize the extraction of contrast. Essentially what happens in the filter is the separation of "packed cells" as in hemoconcentration during surgery. Filter size and geometry can be adopted to optimize the hemoconcentration. Hemoconcentration to the hematocrit levels as high as 90% are possible if a plasma separation membrane is used instead of the high permeability dialysis membrane before replacement solution is added. This will result in small amounts of protein loss that are clinically insignificant.

Figure 10:
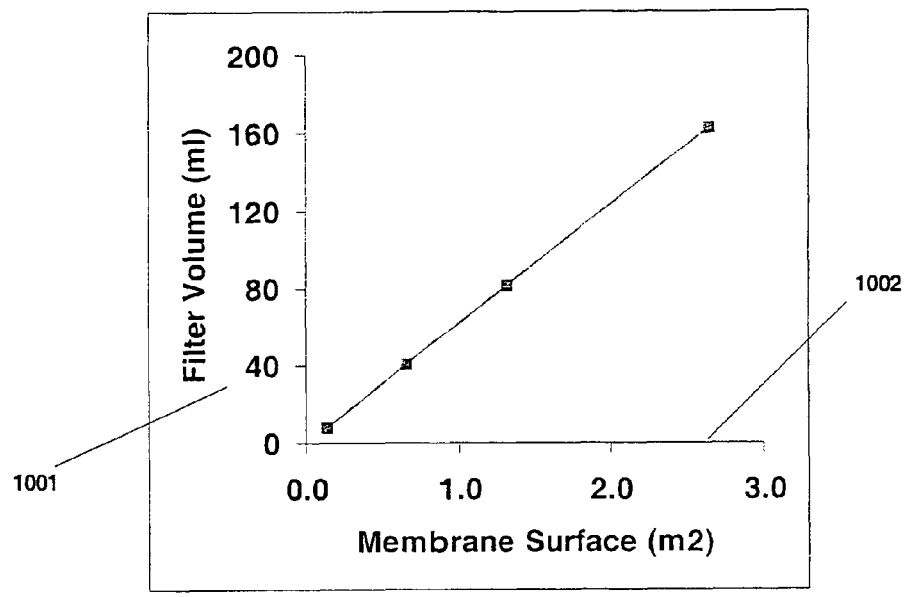
FIG. 10 shows the affect of membrane surface on filter volume.
Figure 11:
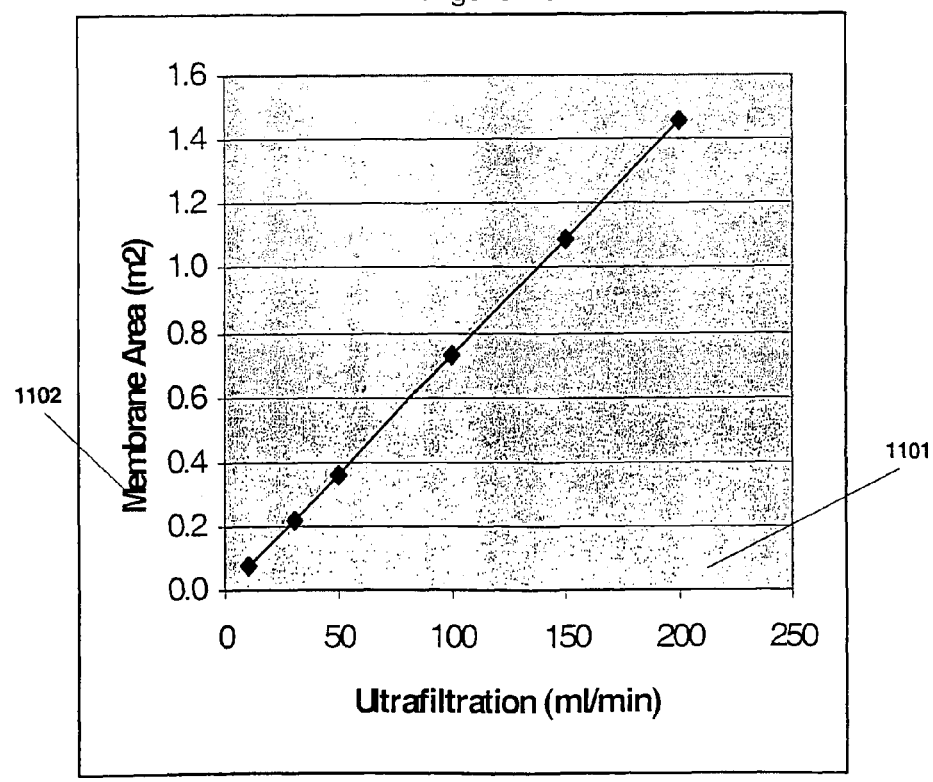
FIG. 11 shows the affect of membrane surface on allowable ultrafiltration rates.

If replacement solution and ultrafiltrate pump are required to operate at 200 ml/min the filter will need to be designed to handle a rather high flux across the membrane. FIGS. 10 and 11 show the effect of flux on the filter design. Fortunately a number of standard filters exist in the range of 0.5 to 2.0 sq. meters that can be used by the device to avoid the expensive tooling. FIG. 10 shows the volume of blood (Filter Volume 1001) in a filter versus the membrane surface 1002 area given a 0.2 mm diameter hollow fiber. For example a 1 m2 filter surface area results in a 63 ml blood volume. FIG. 11 of the same filter shows the maximum ultrafiltration rate 1101 of the same filter versus membrane surface area 1102. A filter with 63 ml blood volume and 1 m2 surface area has a maximum flux rate of 140 ml/min. These ultrafiltration rates are calculated with a Hct of 32%. Higher ultrafiltration rates are possible with lower Hct levels. This will be the case with the contrast removal system if the replacement solution flow rate is set to 200 ml/min. For instance, if the patient' Hct is 34% and the blood flow is 200 ml/min and the replacement solution flow rate is 200 ml/min, then the Hct of the blood entering the filter will be 20.5% Hct.

Figure 13:
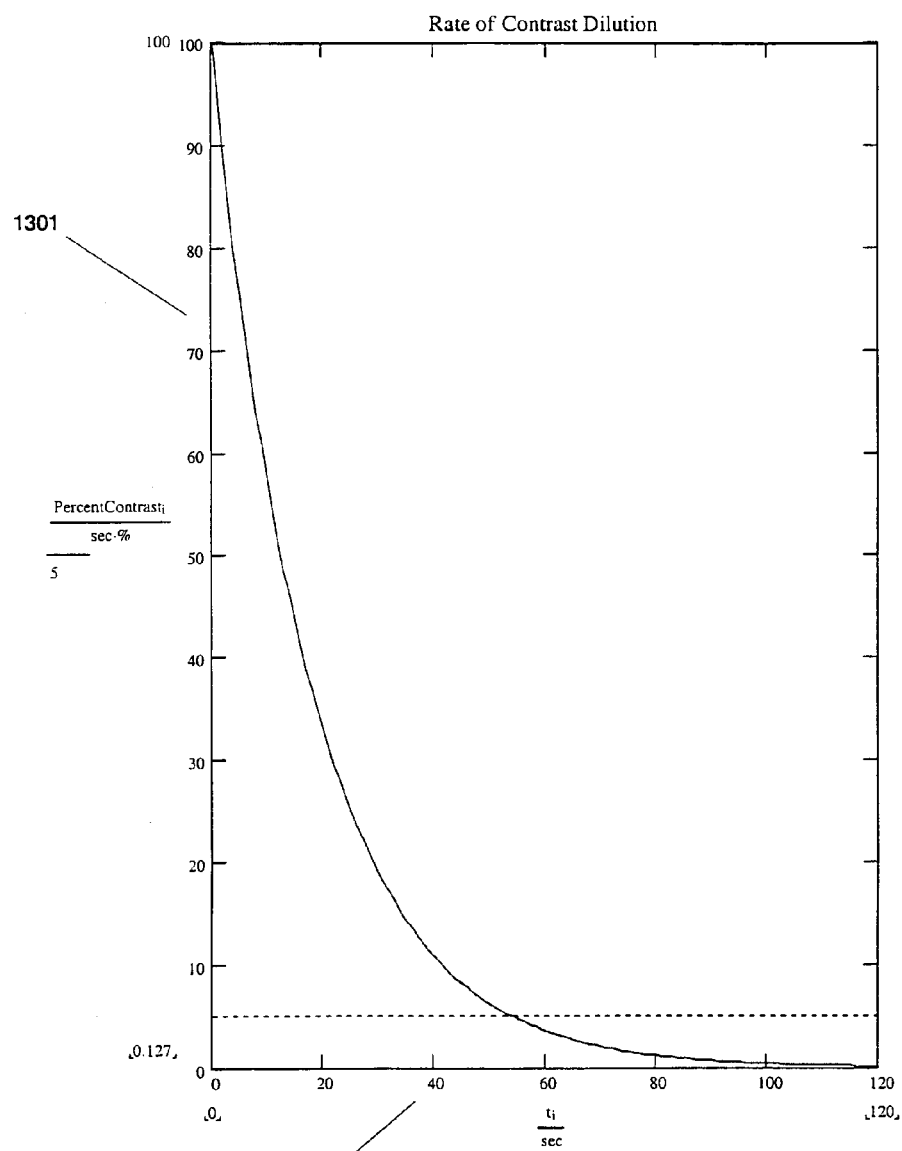
FIG. 13 shows the dilution rate of contrast removal for a 60 ml volume circuit with a replacement solution rate of 200 ml/min.

FIG. 13 shows rate of contrast dilution rate 1301 versus time in minutes 1302 given a filter volume of 60 ml and a replacement solution of 200 ml/min. The time constant, i.e., (how long it takes to remove 63% of the contrast) for the dilution of contrast may be calculated by dividing the volume of the filter by the replacement solution flow rate. This assumes that the contrast bolus has been trapped within the filter. The rate of dilution follows a first order function and may be accurately modeled as such. Where the time constant is 18 seconds, it will take 3 time constants (54 seconds) to remove 95% of the contrast from the bolus. To minimize the amount of replacement fluid used and decrease the dilution time period, the smallest filter volume should be used. If the replacement solution and ultrafiltrate flow rate are reduced to 150 ml/min and a filter volume of 40 ml is chosen, the time constant in this case will be 16 seconds and it will take 3*16 seconds=48 seconds to remove 95% of the contrast in the filter. Such frequent extended periods may have an ischemic effect on the heart so the use of a bypass pump to maintain coronary sinus blood flow is helpful. Generally over 100 ml contrast injections will be performed during a 1 to 2 hr procedure.

Figure 4:
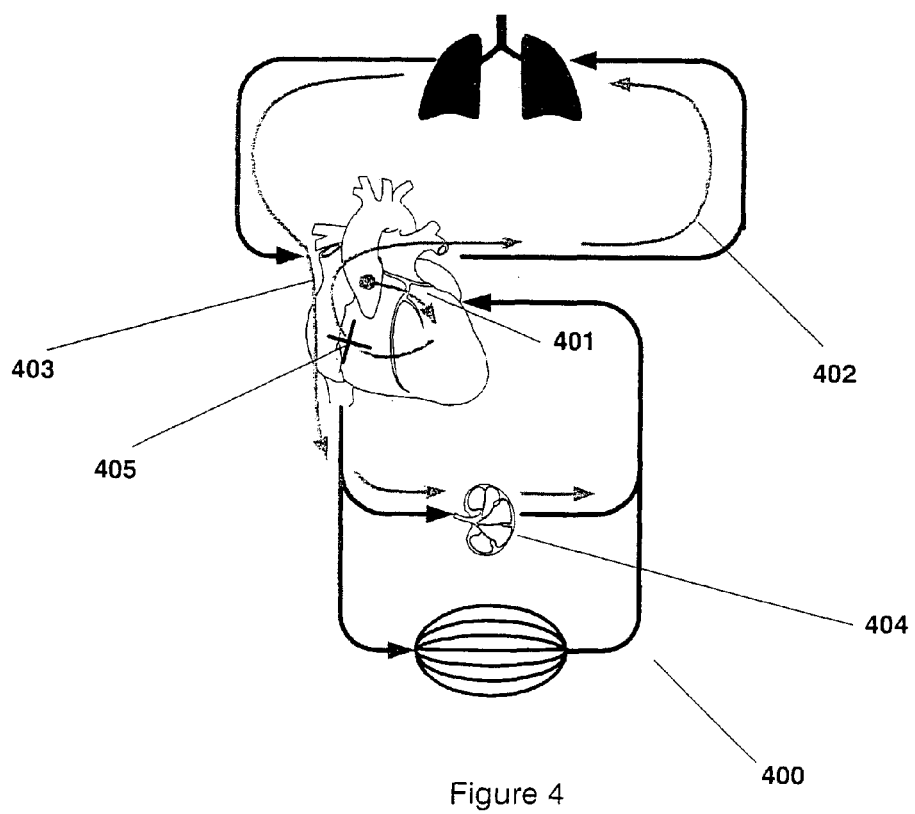
FIG. 4 shows the circulation of contrast in the blood stream when inserted via the coronary artery.

Catheter Design:

FIG. 4 shows the route of contrast after a coronary injection 400. A bolus of contrast travels through the right heart 401, pulmonary circulation 402, left heart 403 and aorta before reaching the kidney 404 on the first pass. The cross 405 points out the coronary sinus where the contrast can be intercepted before it is mixed into the central blood stream. Since coronary contrast injections are most commonly directed into either the left ascending coronary artery (LAD), or left circumflex artery, the entire bolus of contrast (10-15 ml) reemerges in the coronary sinus almost undiluted by blood. The total coronary sinus blood flow in an average person is about 200 ml/min. The coronary sinus empties into the right atrium of the heart (RA) where the contrast bolus is mixed into the stream of venous blood (4,000 ml/min) returning from the peripheral arterial circulation and the brain via vena cava.

Contrast media has high viscosity. Its viscosity rapidly drops with dilution and temperature increase. The table below lists viscosity of the most common contrast media Omnipaque (Iohexol) at different levels of dilution (as marketed) and room and body temperature. The 240 mgI/ml is a common injection concentration. The units of mgI/ml stands for milligrams of iodine per milliliter of drug. In comparison, viscosity of blood is 2.5 to 3.5 cP at normal conditions.

| Concentration | Viscosity (cP) at 20 Deg C. | Viscosity (cP) at 37 Deg C. |
| --- | --- | --- |
| 240 mgI/ml | 5.8 | 3.4 |
| 350 mgI/ml | 20.4 | 10.4 |

Figure 5:
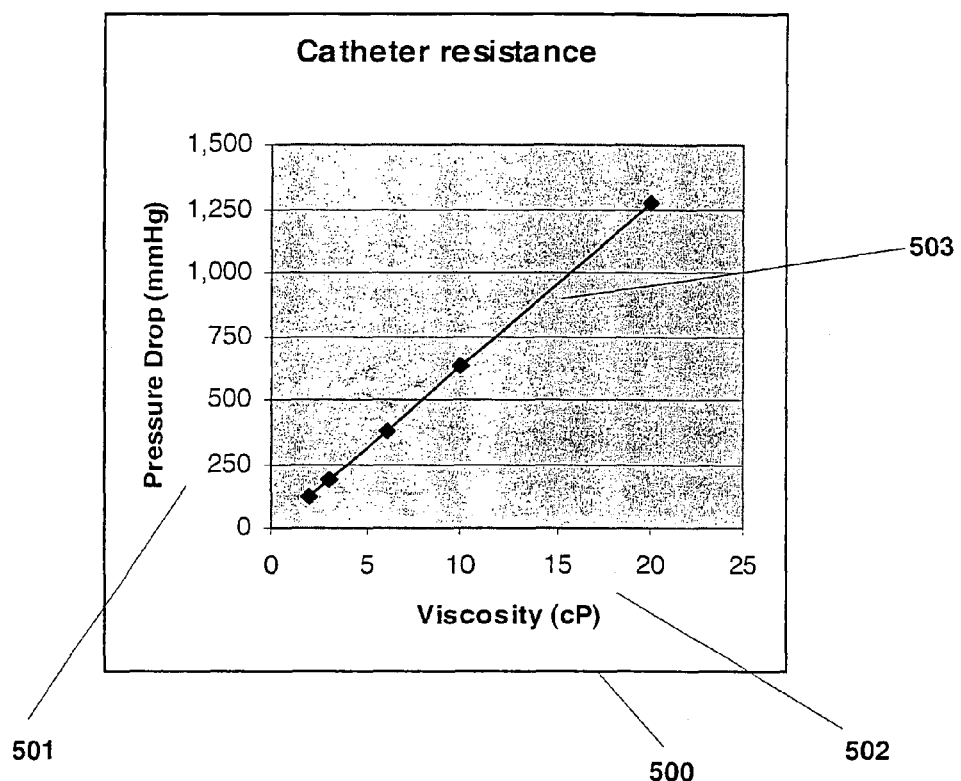
FIG. 5 shows the resistance of the coronary sinus catheter.

FIG. 5 shows a graph of viscosity versus Pressure 500. The pressure 501 required to generate 200 ml/min flow in a catheter lumen with 2.0 mm ID and 1 meter long as a function of the viscosity 502 of pumped fluid is represented by trace 503. The expected viscosity of fluid will directly influence the design of the CS withdrawal catheter. Hoping that the contrast in the CS will be at body temperature designing for the 10 cP viscosity fluid flow seems sufficient. At the same time, the presence of pulsatile flow and an additional design margin for some patients may require instantaneous flows as high as 300 ml/min. It may be that 9 F (3 mm OD) catheters will be required for the femoral approach. Shorter jugular catheters should not be a problem in using either an 8 F or 9 F size.

Contrast Detector:

The contrast sensor 108 is located extracorporeally in the withdrawal line 106 of the blood circuit 100 upstream of the withdrawal blood pumps 103 and 104. Detection of the presence of contrast in blood can be reliably achieved using a photometric hematocrit sensor. When contrast is mixed with blood the Hct is reduced because the percentage of red blood cells to whole blood volume is reduced. This technique has a number of advantages over other methods. It is an optical method and does not require contact with the blood. It is independent of the electrical properties of blood and does not require a radiation source. The sensor was developed for blood volume monitoring. It uses three wavelengths of infrared light to measure oxygen saturation as well as Hct. The measurement of Hct is affected by the oxygen concentration of blood and its effects can be compensated for if three infrared wavelengths are used, preferable 620, 820 and 940 nm. Blood will be diluted by contrast to very high degree making the detection very reliable. Testing has shown that reductions in Hct as lows as 1% may be easily detected.

An alternative approach was also investigated which worked well was the use of a conductivity sensor. Testing was conducted with VISIPAQUE™ which is an isosmolar contrast medium. With an osmolality equal to that of blood, VISIPAQUE™ was designed for patient safety and comfort. VISIPAQUE™ is formulated with sodium and calcium in a ratio equivalent to blood. The contrast solutions of blood and contrast agent tested had higher conductivities than that of blood and the bolus of diluted contrast could also be detected in concentrations as low as 1%. The iodine content in different radiographic contrast media can vary from 11% to 48%. Iodinated contrast agents are classified as ionic or high osmolar contrast media (HOCM) or nonionic or low osmolar contrast media (LOCM).

It is also possible to avoid the requirement for the detection of contrast by having the interventionalist press a foot pedal or hand switch while injecting contrast. This would indicate to the device that a bolus of contrast was being injected when the switch was turned on and cessation had occurred when the switch was turned off. If automated contrast media injection devices such as the Empower CT™ were used for the delivery of contrast the injection switch could be electrically wired to the contrast removal device for the purposes of informing the contrast removal device of the initiation and duration of a contrast injection.

When contrast is detected, filtration starts. It may start somewhat ahead of contrast entering the filter so as not to miss any contrast or if the tubing volume between the contrast detection sensor and the filter is sufficiently large enough a delay may elapse before the device begins contrast dilution. There is no harm in filtering out several milliliters of plasma water. To enable filtration, the prefilter blood pump can be slowed down or stopped altogether while the bypass blood pump flow rate is increased to maintain physiological CS blood flow. Contrast with some plasma and replacement solutions added to it is now diverted into the ultrafiltrate collection bag.

Pressure Controllers:

The contrast removal device uses a pressure controller to prevent complete vein collapse when withdrawing blood and over pressurizations when infusion blood. CS collapse is prevented by reducing the blood withdrawal flow rate in response to a pressure drop in a withdrawal tube. If the vein collapses nevertheless intermittently, the controller facilitates recovery and continues the blood withdrawal. Infusion occlusions are handled in a similar manner, the infusion pressure is continuously measured and used as feedback to keep the infusion pressure within specific pressures limits by reducing blood flow. Since the blood pumps control both the withdrawal and infusion pressure simultaneously a single controller has been devised to reduce flow based upon a pressure excursion in either sensor without resulting in instabilities or abrupt changes in blood flow.

A pressure sensor 110 in the withdrawal tube monitors the blood pressure in real time. If and when a pressure drop is detected which exceeds the specified allowed limit in the withdrawal line, the controller (which receives and processes the pressure sensor signal) slows the blood pump to reduce the flow rate of blood being withdrawn from the peripheral vein. By slowing the withdrawal flow, the pressure in the withdrawal line 106 and CS vein near the catheter may return to a higher level. This pressure increase has been shown to be sufficient to prevent vein collapse, before it actually occurs and allow for a continued withdrawal blood flow (albeit at a reduced withdrawal flow). However, if the pressure in the withdrawal line does not sufficiently elevate and the vein continues to fully collapse, the controller will detect the continued low pressure in the withdrawal line and continue to reduce the pump flow until the pump stops.

The contrast removal system includes two processors 302, 305 and memory for storing data and software control algorithms. The Controller CPU 305 receives input signals from pressure sensors regarding the withdrawal 110 and infusion pressures 121 in the extracorporeal circuit, and from the blood pumps 103, 104 regarding the pump speeds. The Controller CPU processes these input signals, applies the control algorithms and generates control signals that regulate the pump via the motor controller 302 and hence the flow rate of blood and through the circuit.

The controller may regulate blood withdrawn from a CS vein to a flow rate in the range of 0 to 300 ml/min (milliliters per minute). An operator may select a maximum withdrawal flow rate within this normal pressure range via the user setting entry 309 at which the contrast removal system is to operate. The controller will maintain the flow rate at or near the desired flow rate, provided that there is compliance with a pressure versus flow rate limit control algorithms. The controller maintains the withdrawal blood flow rate at the selected maximum flow rate, but automatically reduces the flow rate if the pressure in the system falls below a pressure limit (becomes too negative) for the actual flow rate. Thus, if there develops a partial flow restriction in the withdrawal vein or in the extracorporeal system, the controller will react by reducing the flow rate and track physiological flow.

The controller optimizes blood flow at or below a preset maximum flow rate in accordance with one or more pressure versus flow algorithms. These algorithms may be stored in memory of the controller which includes a processor, e.g., microprocessor; memory for data and program storage; input/output (I/O) devices for interacting with a human operator, for receiving feedback signals, e.g., pressure signals, from the blood circuit and possibly other systems, e.g., patient condition, and for issuing commands to control the pump speed; and data busses to allow the controller components to communicate with one another.

The control algorithms may include (without limitations): maximum flow settings for an individual patient treatment that is entered by the operator, a data listing of acceptable withdrawal/line pressures for each of a series of flow rates, and mathematical equations, e.g., linear, which correlates acceptable pressure to a flow rate. The algorithms may be determined for each particular make or model of an extraction and infusion extracorporeal blood system. In the present embodiment, the pressure versus flow rate curves for occlusion and disconnect for the specified blood circuits are pre-programmed into the system. They may also be calibrated at the start of treatment via the generation of a flow rate versus pressure test before the CS is occluded with the balloon.

Feedback signals are also used by the controller to confirm that the control algorithms are being satisfied. A real time pressure sensor signal from the withdrawal tube may be transmitted (via wire or wireless) to the controller. This pressure signal is applied by the controller as a feedback signal to compare the actual pressure with the pressure limits stored in memory of the controller for the current flow rate through the blood circuit. Based on this comparison, the controller sends control commands to adjust the speed of the pump motor, which controls the withdrawal and infusion pressures in the blood circuit. Using the pressure feedback signal, the controller ensures that the flow rate in the circuit complies with the variable pressure limits. Moreover, the pressure is monitored in real time every 10 ms to 20 ms so that the controller may continually determine whether the flow rate or pressure is acceptable. This is achieved by looking at the average flow rate over a consecutive one second period, and if the flow is less than a preset rate, the pump is stopped.

Figure 6:
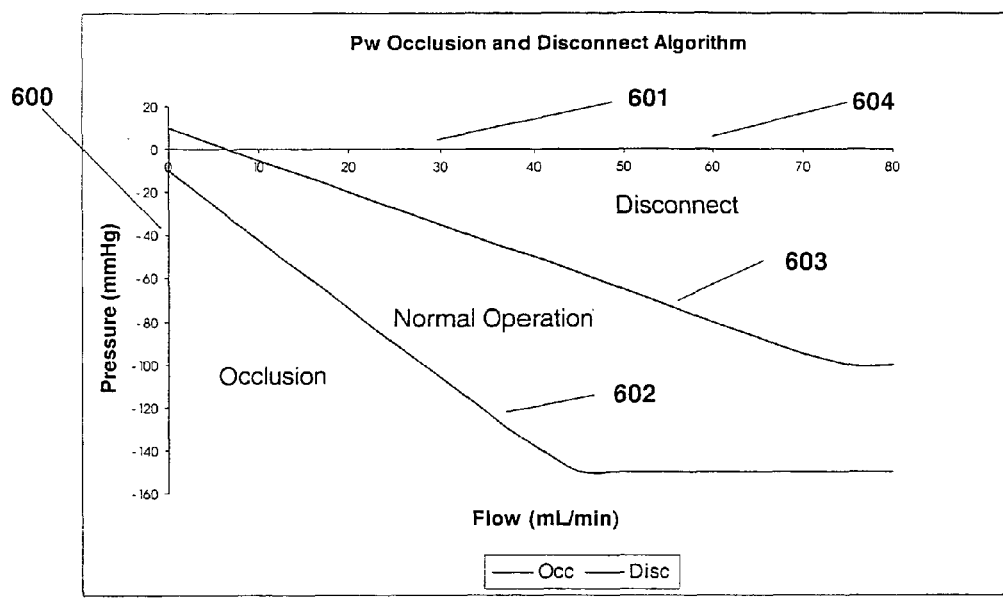
FIG. 6 shows the withdrawal occlusion and disconnect algorithms for the contrast removal device.

FIG. 6 is a chart of withdrawal pressure limits 600 in the blood circuit versus the blood flow rate 601 in the circuit for both occlusion and disconnects. The chart shows graphically exemplary control algorithms for controlling pressure in the withdrawal line as a function of the actual blood flow. The blood flow rate is known, and calculated from the known pump speed. An occlusion control function 602 (PwOcc—Occlusion) provides a variable pressure limit versus flow rate (sloped portion of PwOcc—Occlusion) for controlling the minimum pressure limit in the withdrawal line as a function of flow rate.

The maximum negative pressure (i.e., lowest suction level) in the withdrawal line is limited by an algorithm 603 (disconnect—PwDisc) which is used to sense when a disconnect occurs in the withdrawal line. The withdrawal line has a suction pressure (sub-atmospheric) pressure to draw blood from the CS and is a function of blood flow, blood viscosity and the resistance of the withdrawal line and catheter. This suction pressure is shown as a negative pressure in mmHg in FIG. 6. If the actual suction pressure rises above a limit (PwDisc), then the controller may signal that a disconnect has occurred, especially if air is also detected in the blood circuit. The suction pressure in the withdrawal line is controlled to be between the occlusion and disconnect pressure limits 602, 603.

The maximum withdrawal resistance (PwOcc, —see the slope of line 602) for a given flow rate is described by the occlusion algorithm curve 602. This allowable occlusion pressure, PwOcc increases as blood flow increases. This increase may be represented by a linear slope of flow rate versus pressure, that continues, until a maximum flow rate 604 is reached. The occlusion algorithm curve is based on theoretical and empirical data with a blood Hct of 50% (maximum Hct expected in clinical operation), and the maximum expected resistance of the withdrawal catheter and withdrawal blood circuit tube expected during normal operation when measured at Pw.

The withdrawal pressure sensor signal (Pw) is also applied to determine whether a disconnection has occurred in the withdrawal blood circuit between the withdrawal tubing 106 from the balloon catheter 102 or a rupture in the withdrawal tubing. The control algorithm for detecting a disconnection is represented by PwDisc curve 603. This curve 603 represents the minimum resistance of the balloon catheter and withdrawal tubing, with a blood Hct of 25% (minimum Hct expected in clinical operation), at a temperature of 37° C. The data to generate this curve 603 may be obtained in vitro and later incorporated in the controller software.

During the device operation the measured withdrawal pressure (Pw) is evaluated in real time, for example, every 10 to 20 milliseconds, by the pressure controller. Measured Pw is compared to the point on the curve 603 that corresponds to the current blood flow rate. A disconnection is detected when the pressure Pw at a given blood flow is greater than the pressure described by curve 603, or if air is detected in the blood circuit. If the withdrawal line becomes disconnected, the blood pumps 103 and 104 will entrain air into the tubing due to the suction caused by the withdrawal pressure (Pw) when the blood pumps are withdrawing blood. The pressure measured by the withdrawal pressure transducer Pw will increase (become less negative) in the presence of a disconnection because the resistance of the withdrawal line will decrease.

Figure 7:
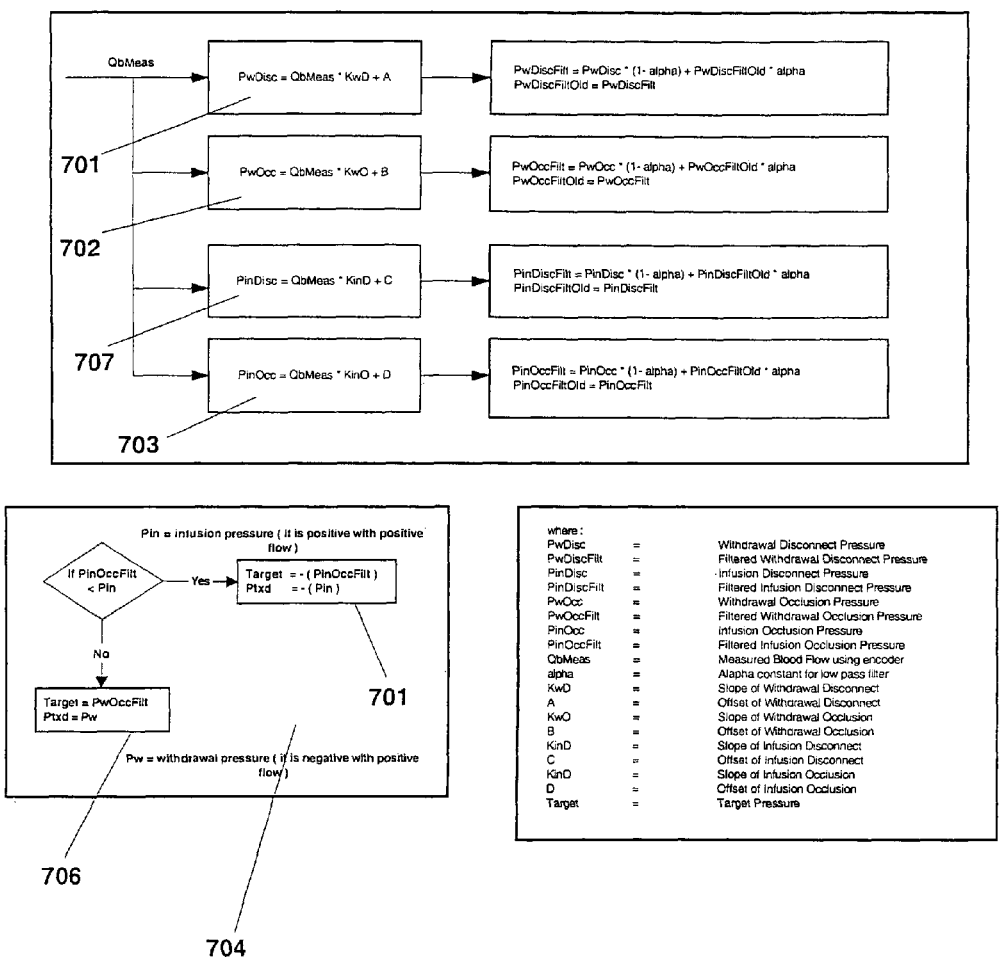
FIG. 7 shows how the various withdrawal and infusion occlusion and disconnect limits are calculated based upon flow as well as how the target pressure trajectory is determined.

FIG. 7 is a flow chart showing in mathematical terms the control algorithms shown in FIG. 6. The allowable occlusion pressure (PwOcc) 601 is determined as a function of blood flow (QbMeas). The blood flow (QbMeas) may be determined by the controller, e.g., controller CPU, based on the rotational speed of the blood pumps (Prefilter blood pump and bypass blood pump) and the known volume of blood that is pumped with each rotation of that pump, as is shown in the equation below:

$$PwOcc = Qb\text{Meas} * KwO + B$$

Where QbMeas is the measured blood flow, KwO is the withdrawal occlusion control algorithm 602, e.g., a linear slope of flow vs. pressure, and B is a pressure offset applied to the withdrawal occlusion, which offset is described below 702.

The expression presented here for PwOcc 702 is a linear equation. PwOcc may also be implemented as a look up table where a known QbMeas is entered to obtain a value for PwOcc. In addition, the expression for PwOcc may be a second order polynomial in the presence of turbulent flow. The expression for PwOcc to be chosen in a particular implementation will be based upon the characteristics of the tube and the presence of laminar or turbulent flow.

The PwOcc signal may be filtered with a 0.2 Hz low pass filter to avoid false occlusion alarms, as indicated in the following sequential pair of equations.

PwOccFilt = PwOcc * (1− alpha) + PwOccFiltOld * alpha
Where alpha = exp(−t/Tau)
Where t = discrete real time sample interval in seconds and
The time constant Tau = 1/(2 * PI * Fc)

Where PI=3.1416 and Fc is equal to the cutoff frequency of the first order low pass filter in Hz. Thus, for a 0.2 Hx filter, Tau=0.7957 therefore alpha=0.9875. Where PwOccFilt is the current calculated occlusion pressure limit for the actual flow rate, after being filtered. PwOccFiltOld is the previous calculated occlusion pressure, and "alpha" is a constant of the low pass filter. Thus, PwOccFiltOld=PwOccFilt, for each successive determination of PwOccfilt.

Similar determinations are made for the calculated pressure limits for the filtered withdrawal disconnect limit (PwDiscFilt), filtered infusion disconnect limit (PinDiscFilt) and filtered infusion occlusion limit (PinOccFilt).

The PwDisc curve 603, shown in FIG. 6 is described in equation form below and shown in 701 of FIG. 7. The withdrawal disconnection pressure 702, PwDisc is calculated as a function (KwD) of blood flow, QbMeas which is measured blood flow calculated from the encoder blood pump speed signals.

QbMeas=Q1+Q2 where Q1 is the measured prefilter blood pump flow and Q2 is the measured bypass blood pump flow.

$$PwDisc = QbMeas * KwD + A$$

Where A is a pressure constant offset, and KwD represents the slope of the PwDisc curve 603. In addition, the PwDisc (withdrawal pressure limit for disconnect) is filtered with a 0.2 Hz low pass filter to avoid false disconnect alarms, reference 701 in FIG. 7.

PwDisc 701 is a linear equation but may be implemented as a look up table where a known QbMeas is entered to obtain a value for QbMeas. In addition, the expression for PwDisc may be a second order polynomial in the presence of turbulent flow. The expression for PwDisc to be chosen in a particular implementation will be based upon the characteristics of the tube and the presence of laminar or turbulent flow.

PwDiscFilt = PwDisc * (1− alpha) + PwDiscFiltOld * alpha
PwDiscFiltOld = PwDiscFilt Where alpha is a function of the filter.

The air detector 111 detects the presence of air when entrained. If the withdrawal pressure (Pw) exceeds (is less negative than) the disconnect pressure (PwDisc) 603 AND air is detected in the blood circuit by the air detector, then the controller declares a withdrawal disconnection, and the blood pump and the ultrafiltrate pump are immediately stopped.

This logic function is expressed as:

If (Pw>PwDiscFilt AND AirDetected=TRUE)

{then Declare a withdrawal disconnect}

The above logic function is a reliable detection of a withdrawal line disconnection, while avoiding false alarms due to blood pressure measurements with blood pressure cuffs. For example, a false alarm could be generated when blood pressure cuffs are pressurized which causes an increased venous pressure and in turn lower withdrawal pressure. The lower withdrawal pressure caused by a blood pressure cuff might be interpreted by the controller as a disconnection resulting in false alarms, except for the logic requirement of air being detected.

Figure 9:
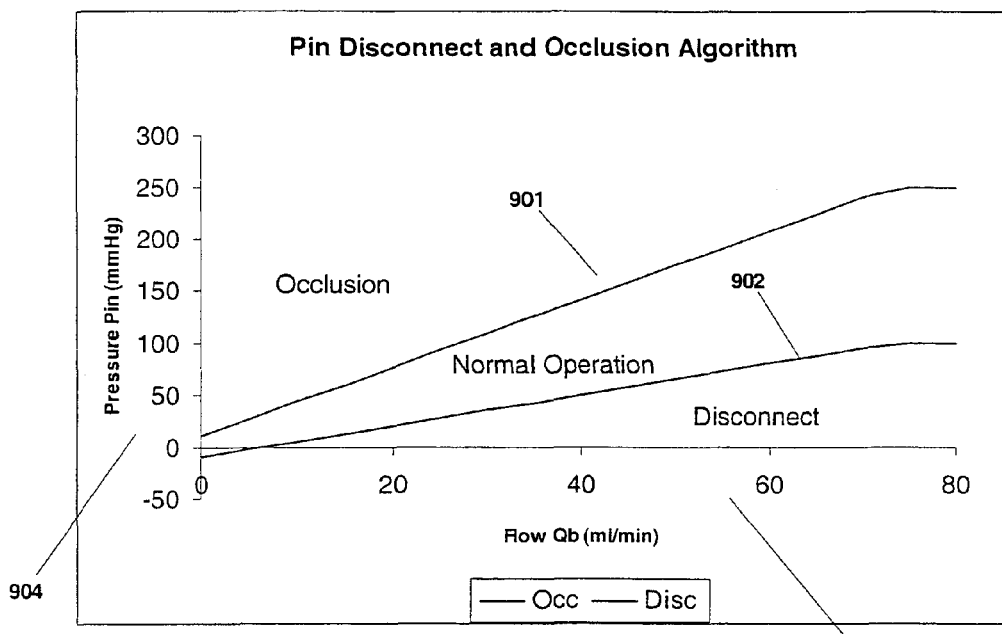
FIG. 9 shows the infusion occlusion and disconnect algorithms for the contrast removal device.

The occlusion and disconnect pressure limits for the return (infusion) line are graphically shown in FIG. 9. These calculations are made in a similar manner as described above for determining PwOccFilt. The infusion-occlusion pressure limit (PinOcc) 901 (FIG. 9) is calculated as a function of blood flow (QbMeas) where QbMeas is actual blood flow calculated from the pump speed feedback signal.

PinOcc=QbMeas*KwO+B, where KwO is the factor for converting (see FIG. 9, Occlusion line 901) the actual blood flow rate 903 to a pressure limit 904. The expression to describe PinOcc 901 is a linear equation. PinOcc may also be implemented as a look up table where a known QbMeas is entered to obtain a value for PinOcc. In addition, the expression for PinOcc may be a second order polynomial in the presence of turbulent flow. The expression for PinOcc to be chosen in a particular implementation will be based upon the characteristics of the tube and the presence of laminar or turbulent flow.

PinOcc is filtered with a 0.2 Hz low pass filter to avoid false disconnect alarms.

PinOccFilt = PinOcc * (1− alpha) + PinOccFiltOld * alpha
PinOccFiltOld = PinOccFilt FIG. 7 also shows the interaction of the control algorithms for withdrawal occlusion (PwOccFilt) and the infusion occlusion (PinOccFilt). The control algorithm for having two control algorithms applicable to determining the proper flow rate is that only one of the control algorithms will be applied to determine a target flow rate at any one time. To select which algorithm to use, the controller performs a logical "If-Then operation" 704 that determines whether the target is to be the withdrawal occlusion 706 or infusion occlusion algorithms 705. The criteria for the If-Then operation is whether the infusion line is occluded or not. If the infusion line is occluded, Pin is greater than PinOccFilt; therefore, the Target is set to PinOccFilt. Thus the infusion occlusion algorithm will only be enabled if there is an infusion occlusion present.

Figure 8:
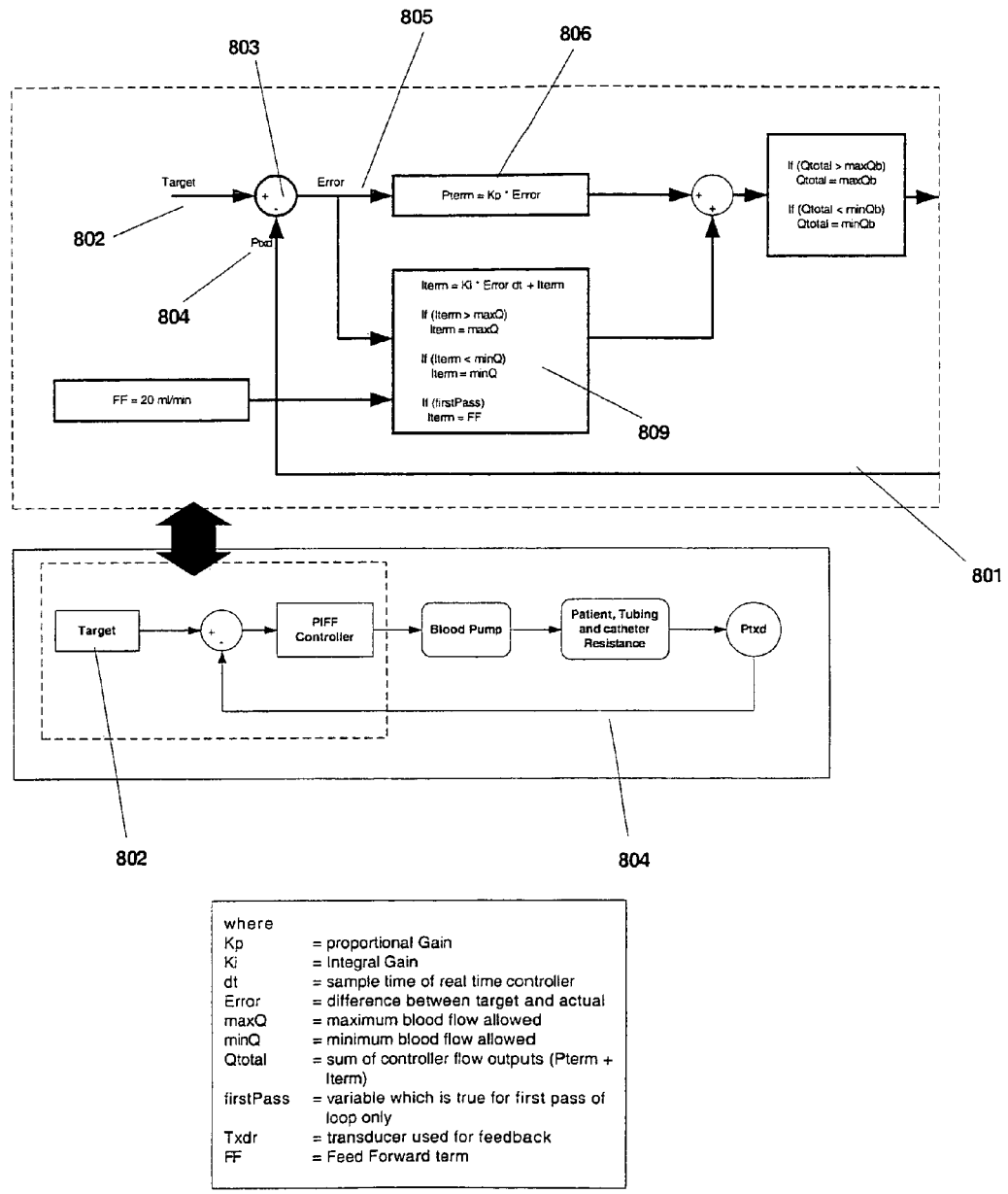
FIG. 8 shows how the PIFF algorithm is implemented.

In particular, the infusion occlusion algorithm (PinOccFilt) is the target (Target) and infusion pressure (Pin) is applied as a feedback signal (Ptxd) 804 (FIG. 8), only when the infusion pressure (Pin) exceeds the occlusion limit for infusion pressure (PinOccFilt). This algorithm is shown in FIG. 8. Otherwise, the Target 802 is the occlusion withdrawal pressure limit (PwOccFilt) and the feedback signal is the withdrawal pressure (Pw).

The If-Then (704) algorithm is set forth below in a logic statement.

```
If(PinOccFilt < Pin)
   {Then Target = –( PinOccFilt ), and Ptxd = –(Pin )}
   {Else Target = PwOccFilt and Ptxd = Pw }
```

A pressure controller as outlined in FIG. 8 may be used to control the Ptxd 804 measurement to the Target pressure 802. The Target pressure will be either the PinOccFilt or PwOccFilt limit based upon the IF statement described above.

FIG. 8 includes a functional diagram of a PIFF (Proportional Integral Feed Forward) pressure controller 801 for the contrast removal apparatus 100, and shows how the PIFF operates to control pressure and flow of blood through the circuit. Controllers of the PIFF type are well known in the field of "controls engineering". The PIFF pressure controller 801 controls the withdrawal pressure to the prescribed target pressure 802, which is the filtered withdrawal occlusion pressure limit (PwOccFilt), by adjusting the filter and bypass blood pump flow rate. The PIFF may alternatively use as a target the limit for infusion pressure (PinOccFilt). The target pressure 802 limit is compared 803 to a corresponding actual pressure 804, which is withdrawal pressure (Pw) if the target is PwOccFilt and is infusion pressure (Pin) if the target is PinOccFilt. The actual pressure is applied as a feedback signal (Ptxd) in the PIFF. The logical compare operation 803 generates a difference signal (Error) 805 that is processed by the PIFF.

The PIFF determines the appropriate total flow rate (Qtotal) based on the difference signal 805, the current total blood flow rate and the flow rate limit. Note that Qtotal=Q1+Q2 where Q1 equals the prefilter blood pump flow rate and Q2 equals the bypass blood pump flow rate. The PIFF evaluates the difference between the target pressure limit and actual pressure (feedback) with a proportional gain (Kp), an integral gain (Ki) and a feed forward term (FF) 809. The proportional gain (Kp) represents the gain applied to current value of the error signal 805 to generate a proportional term (Pterm) 806, which is one component of the sum of the current desired flow (Qtotal). The integral gain (Ki) is the other component of Qtotal, and is a gain applied to the rate at which the error signal varies with time (error dt). The product of the integral gain and the error dt (Iterm) is summed with the previous value of Iterm to generate a current item value. The current Iterm value and Pterm value are summed, checked to ensure that the sum is within flow limits, and applied as the current desired total flow rate (Qtotal). This desired flow rate (Qtotal) is then applied to control the prefilter and bypass blood pump speeds, and, in turn, the actual flow rate through the blood circuit.

As stated earlier the blood pumps have three basic flow configurations, waiting for contrast detection, contrast detected and contrast removal in process. If the system is waiting for a contrast detection then Q1=0.8*Qtotal and Q2=0.2*Qtotal. If the system has just detected contrast then Q1=1*Qtotal and Q2=0*Qtotal until the contrast bolus has been deposited into the filter. This time period can be based upon an elapsed time period after the initial detection of contrast, volume displaced by the prefilter blood pump after the detection of contrast based, contrast level detected by the contrast sensor based, injector input based or a combination of the aforementioned. If the system is in the contrast removal process and the bolus is now within the filter Q1=0.2*Qtotal and Q2=0.8*Qtotal.

The gain of the PIFF pressure controller Kp and Ki have been chosen to ensure stability when controlling with both withdrawal and infusion pressures. The same PIFF controller is used for limiting withdrawal and infusion pressures. None of the controller terms are reset when the targets and feedback transducers are switched. This ensures that there are no discontinuities in blood flow and that transitions between control inputs are smooth and free from oscillation. Thus, when the PIFF pressure controller switches from controlling on withdrawal pressure top infusion pressure the blood pump does not stop, it continues at a velocity dictated by the pressure control algorithm.

The proportional and integral gains (Kp and Ki) of the pressure controller are selected to ensure stability. Kp 806 and Ki 809 were chosen to ensure that pressure overshoots are less than 30 mmHg, and that the pressure waveform when viewed on a data acquisition system was smooth and free of noise. In general Kp may be increased until the noise level on the signal being controlled exceeds the desired level. Kp is then reduced by 30%. Ki is chosen to ensure the steady state error is eliminated and that overshoot is minimized. Both the integral term and the total flow output, Qtotal of the PIFF controller are limited to a maximum of 300 ml/min, in this embodiment. The limit may also be adjusted based upon user input via the user setting entry 309.

In addition, in this embodiment the flow limits for the integral term and total flow output may be increased linearly starting at a maximum rate of 20 ml/min (FF). When the PIFF controller is initially started, the integral term (Iterm) is set equal to the feed forward term (FF), which may be 20 ml/min. Thus, 40 seconds are required to increase the flow limit from an initial setting (20 ml/min) to the maximum value of 300 ml/min. This 40 second flow increase period should be sufficient to allow the CS vein to respond to increases in withdrawal flow rate. Limiting the rate of increase of the blood flow is needed because veins are reservoirs of blood and act as hydraulic capacitors. If a flow rate is increased too quickly, then a false high flow of blood can occur for short periods of time because flow may be supplied by the elastance of the vein (that determines compliance), and may not be true sustainable continuous flow much like an electrical capacitor will supply short surges in current. This flow limitation (ramp in flow) is only present for the first 40 seconds of therapy. After this time period has elapsed maximum acceleration in flow ramps are allowed and are only limited by the frequency response of the motor and controller.

This PIFF pressure controller controls pressure in real time, and will immediately reduce the pressure target if a reduction in flow occurs due to an occlusion. The target pressure is reduced in order to comply with the occlusion pressure limit, such as is shown in FIG. 6 and FIG. 9. Reducing the pressure target in the presence of an occlusion will lead to a further reduction in flow, which will result in a further reduction in the target pressure. This process limits the magnitude and duration of negative pressure excursions on the withdrawal side, and, therefore, exposure of the patient's CS to trauma. It also gives the withdrawal (or infusion) vein time to recover, and the patient's CS time to reestablish flow without declaring an occlusion.

When a withdrawal vein collapses, the blood pump will be stopped by the PIFF controller because the vein will have infinite resistance resulting in zero blood flow no matter to what pressure Pw is controlled, at 0 ml/min the target pressure for Pw will be –10 mmHg. The CS will quickly reestablish blood flow and the controller will automatically start withdrawing and infusion blood because the pressure limitation will no longer be valid.

The PIFF applies a maximum withdrawal flow rate (maxQb) and a minimum withdrawal flow rate (minQb). These flow rate boundaries are applied as limits to both the integration term (Item) and the sum of the flow outputs (Qtotal). The maximum withdrawal rate is limited to, e.g., 300 ml/min, to avoid excessive withdrawal flows that might collapse the CS. The minimum flow rate (minQb) is applied to the output flow to ensure that the pump does not retract at a flow rate higher than −20 ml/min. In addition, if the actual flow rate (Qb) drops below a predetermined rate for a certain period of time, e.g., 50 ml/min for 10 seconds, both blood pumps are stopped for a period of 2 seconds to allow CS blood flow to establish. An occluded CS is capable of being pressurized to greater than 35 mm Hg by the coronary artery. It is not necessary to stop the replacement solution pump and the ultrafiltrate pump if they are in operation because both pumps are controlled to match each other flow rate and the net effect is 0 ml/min in or out of the blood path of the filter.

The controller will try and maintain a CS blood flow at maxQb but if the withdrawal resistance experienced by the controller exceeds that specified by the allowable pressure limits flow will be reduced. This results in the controller tracking the maximum flow available from the CS because the pressure limit will not be exceeded until a flow limitation is reached.

CS access presents unique problems that make it difficult for a blood withdrawal controller to maintain constant flow and to not create hazards for the patient. Contrast is being injected into the coronary artery via a catheter which is partially occluding the coronary artery blood flow and thus reducing the coronary vein blood flow which exits via the CS. This creates additional resistance which will vary depending upon catheter position reducing the amount of blood flow through the coronary artery. The controller described herein adjusts the blood flow rate through the extracorporeal circuit to accommodate for such pressure changes and ensure that the changes do not violate the pressure limits set in the controller. As the flow through the withdrawal catheter decreases, the controller reduces pump speed to reduce the withdrawal pressure level. Moreover, the blood infusion side of the blood circulation circuit may involve similar pressure variances. These infusion side pressure changes are also monitored by the controller which may adjust the pump flow rate to accommodate such changes.

In some cases, blood flow can be temporarily impeded by the collapse of the withdrawal vein caused by the patient motion. In other cases CS blood flow may vary physiologically. The software algorithms enable the controller to adjust the withdrawal flow rate of blood to prevent or recover from the collapse of the vein and reestablish the blood flow based on the signal from the withdrawal pressure sensor.

A similar risk of disconnection exists when returning the patient's blood. The infusion needle or the infusion tube between the outlet of the infusion pressure transducer (Pin) and needle may become disconnected during operation. A similar disconnection algorithm (as described for the withdrawal side) is used for detecting the presence of disconnections on the infusion side. Since the blood is being infused the pressures measured by the infusion pressure transducer Pin are positive. The magnitude of Pin will decrease in the presence of a disconnection due to a decrease in the resistance of the infusion line.

A disconnection is detected when the pressure Pin at a given blood flow is less than the pressure described by curve 902 (FIG. 9) for the same said blood flow. The minimum resistance of the 14 Gage cannulae and infusion tubing, with a blood Hct of 25%, at a temperature of 37° C. are represented by the curve 902. The curve 902, shown in FIG. 9 is described in equation form in 707 (FIG. 7). The infusion disconnection pressure, PinDisc 706 is calculated as a function of blood flow, QbMeas where QbMeas, is actual blood flow calculated from the encoder velocities 321, 306 (FIG. 3) of the bypass blood pump 103 and prefilter blood pump 104 (FIG. 1).

$$PinDisc = QbMeas * KinD + C$$

PinDisc is filtered with a 0.2 Hz low pass filter to avoid false disconnection alarms, reference 706 FIG. 7. The present embodiment uses a linear equation to describe PinDisc, but this equation could also be implemented as a look-up table or a second order polynomial in the presence of turbulent flow. The implementation chosen will be based upon the characteristics of the tube and the presence of laminar or turbulent flow.

```
PinDiscFilt = PinDisc * (1− alpha) + PinDiscFiltOld * alpha
PinDiscFiltOld = PinDiscFilt
```

If Pin is less than PinDiscFilt for 2 seconds consecutively, an infusion disconnect is declared and the blood pump and ultrafiltrate pump are immediately stopped.

```
If (Pin > PinDiscFilt)
  {Then Increment Infusion Disconnect Timer}
  {else Reset Infusion Disconnect Timer}
If (Reset Infusion Disconnect Timer = 2 seconds)
  {then Declare Infusion Disconnection}
```

The withdrawal and infusion occlusion detection algorithms use similar methods of detection. Only the specific coefficients describing the maximum and minimum allowable resistances are different.

The purpose of the withdrawal occlusion algorithm is to limit the pressure in the withdrawal vein from becoming negative. A negative pressure in the CS vein may cause it to collapse. The CS pressure is normally 5 mm Hg and it will remain positive as long as the flow in the vein is greater than the flow extracted by the blood pump.

If the resistance of the withdrawal catheter and blood circuit tube are known, the withdrawal flow may be controlled by targeting a specific withdrawal pressure as a function of desired flow and known resistance. For example, assume that the resistance of the withdrawal catheter to blood flow is R and that R equals −1 mm Hg/ml/min. In order for 60 ml/min of blood to flow through the catheter, a pressure drop of 60 mm Hg is required. The pressure may be either positive, pushing blood through the catheter or negative, withdrawing blood through the catheter. On the withdrawal side of the catheter, if a pressure of −60 mm Hg is targeted a blood flow of 60 ml/min will result.

If the flow controller is designed to be based upon resistance, the pressure target required to give the desired flow rate Q would be R*Q. Thus, if a flow of 2-ml/min were required, a pressure of −200 mm Hg would be required as the pressure target for the resistance R described. Since the system knows withdrawal flow based upon encoder velocity and is measuring withdrawal pressure, the system is able to measure the actual withdrawal resistance of the catheter in real time.

If a maximum resistance limit is placed on the withdrawal catheter of −1.1 mm Hg/ml/min, the pressure controller will stop withdrawing flow in the presence of an occlusion. Occlusion can be in the circuit or caused by the vein collapse. The resistance limit is implemented as a maximum pressure allowed for a given flow. Thus, for a resistance limit of −1.1 mm Hg, if the flow drops to 30 ml/min when the current withdrawal pressure is −60 mm Hg in the presence of an occlusion, the maximum pressure allowed is 30 ml/min*−1.1 mm Hg/ml/min=33 mm Hg. This means that the occlusion resistance is −60/30=−2 mm Hg/ml/min. If the occlusion persists when the withdrawal pressure drops to −33 mm Hg, the flow will be reduced to 16.5 ml/min. This will result in a new pressure target of −18.15 mm Hg and so on until the flow stops.

The actual pressure target to deliver the desired flow is difficult to ascertain in advance because of the myriad of variables which effect resistance, blood Hct, needle size within and length within the expected tolerance levels, etc. Instead, the pressure controller targets the maximum resistance allowed, and the flow is limited by the maximum flow output allowed by the pressure controller.

A goal of the control algorithm is to ensure that the pressure at the withdrawal vein never falls below 0 mmHg where vein collapse could occur, or that the infusion pressure exceeds a value that could cause extravasation. If the critical pressure-flow curve is generated at the worst case conditions (highest blood viscosity), the controller will ensure that the pressure in the vein is always above the collapse level or below the extravasation level.

Figure 12:
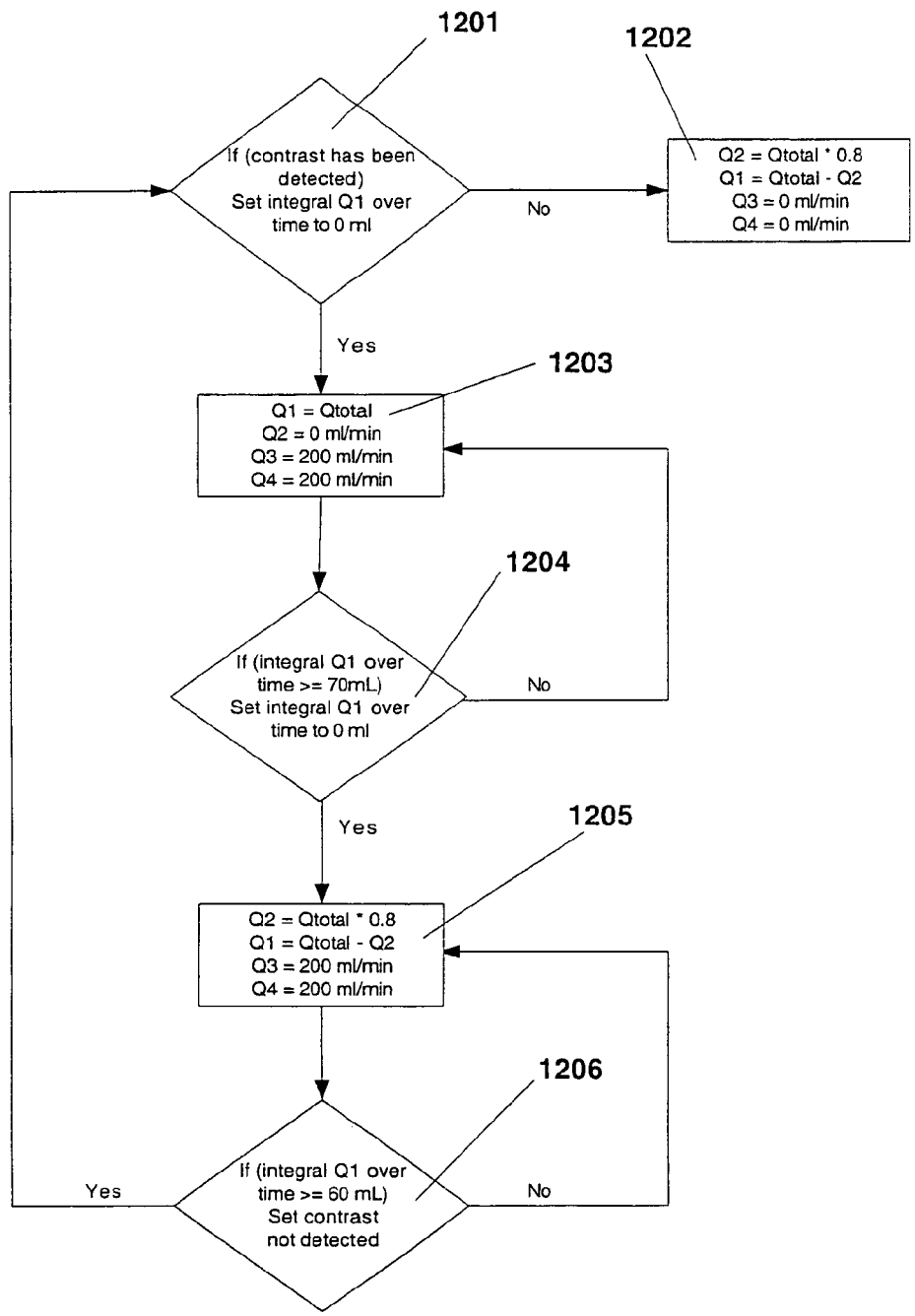
FIG. 12 shows the flow chart for contrast removal.

Contrast Dilution:

FIG. 12 shows a flow chart of an algorithm for the contrast removal algorithm. If contrast has not been detected 1202 the prefilter blood pump Q2 operates at 0.8 times the Qtotal and Q1 the bypass blood pump operates at the difference between Qtotal and Q2. Both the replacement solution Q3 and the ultrafiltrate Q4 pumps are set to 0 ml/min. Every sample interval of the controller the volume displaced by Q1 is set to 0 ml because it has not displaced any volume of contrast into the filter. This is indicated in 1201 as setting the integral of Q1 to 0 ml. Once contrast has been detected the bypass blood pump Q2 is set to 0 ml/min and Q1 is set to Qtotal. Thus all of the contrast is now being entrained by the filter. At the same time the replacement solution and ultrafiltrate pumps are started at their set dilution and extraction rates. In this example 200 ml/min is used. Once the prefilter blood pump Q1 has displaced 70 ml 1204 the contrast and blood solution are now entrained within the 60 ml filter (assuming 10 ml between the filter pump outlet and the inlet to the filter) the bypass blood pump is set to 80% of Qtotal prefilter blood pump Q1 is set to 20% of Qtotal. The replacement solution and ultrafiltrate pumps are left unchanged. Dilution and ultrafiltration will continue to occur until 60 ml of fluid has been pumped by the prefilter blood pump at its lower speed. At this point in time the contrast flag used in software is set to contrast has not been detected and the process begins again.

Because the replacement solution pump and the ultrafiltrate pump are matched in flow they play no part in the pressure measured at Pw or Pin. They do effect the pre filter pressure Pp and the ultrafiltrate pressure Puf increasing the TMP (Trans membrane pressure) experienced by the filter when the pumps are operational.

In the event of an occlusion in either the withdrawal of infusion line the Qtotal as previously described in FIG. 8 would be reduced. The proportion of the blood flow Qtotal controlled by the bypass blood pump and the prefilter blood pump would be left unchanged. Qtotal is the output flow command for the pressure controller as described in FIG. 8.

Weight Scale Controllers:

The purpose of the weight scale controller is to ensure that the replacement solution flow rate matches the ultrafiltrate flow rate and that the patient does not become hypovolemic or hypervolemic due to incorrect matching of pump flow rates. Peristaltic pumps are generally designed to have a flow accuracy of +/−10%. This accuracy limitation is not due to the accuracy of the motor controller which typically is much better than +/−0.5% of setting but due to variations that occur in the tubing cross-sectional area that result from manufacturing and operational variances. A peristaltic pump operates on the principal that when the tubing loop is depressed and released it will reconstitute back to its original cross-sectional area and entrain fluid as a result of the negative pressure generated by such an action. The resilience and speed of tubing reconstitution after compression of a tube loop is a function of its material properties such as durometer, elasticity, Young's modulus, age, frequency response of tubing, pressure etc. Variances will occur in these properties from batch to batch manufactured and in the pressure conditions experienced which result in variances in the cross-sectional area that the tube reforms to after a depression by a peristaltic pump roller. These variances result in flow errors, so in theory if two pumps have an accuracy of +/−10% worst case under all operating conditions then the maximum mismatch in flow between the two pumps will be 20%. This assumes that one pump operates at the lower limit and the other at the higher limit. At a fluid replacement rate of 200 ml/min this would result in a possible mismatch of 40 ml/min which would be clinically unacceptable. In order to avoid this problem a controller has been devised which eliminates this possibility. Since the purpose of the contrast removal system is to dilute the contrast within the filter and not to add or subtract ultrafiltrate form the patient the weight scale controller targets the measured weight to be equal to the weight of the replacement solution bag added at the start of treatment.

Figure 14:
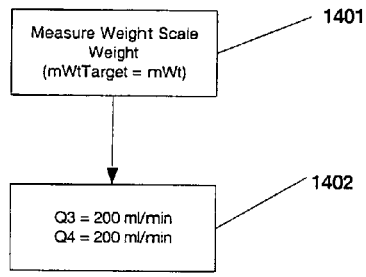
FIG. 14 is a flow chart showing how the weight scale controller is set.

FIG. 14 shows how the target weight is determined before the replacement solution and ultrafiltrate pump are started. Solutions may be added or subtracted during therapy so a new target is established each time dilution is started. mWtTarget is set to the measured weight mWt 1401 by the weight scale before the replacement solution of ultrafiltrate pump are started. mWtTarget is now used for comparison to mWt to determine if the ultrafiltrate pump should be increased or decreased. The controller does not adjust the rate of the replacement solution pump flow rate, it only varies the ultrafiltrate pump flow rate. It sets the rate replacement solution pump flow rate to say 200 ml/min 1402 and then adjusts the ultrafiltration pump to ensure that mWt remains equal to mWtTarget.

Figure 15:
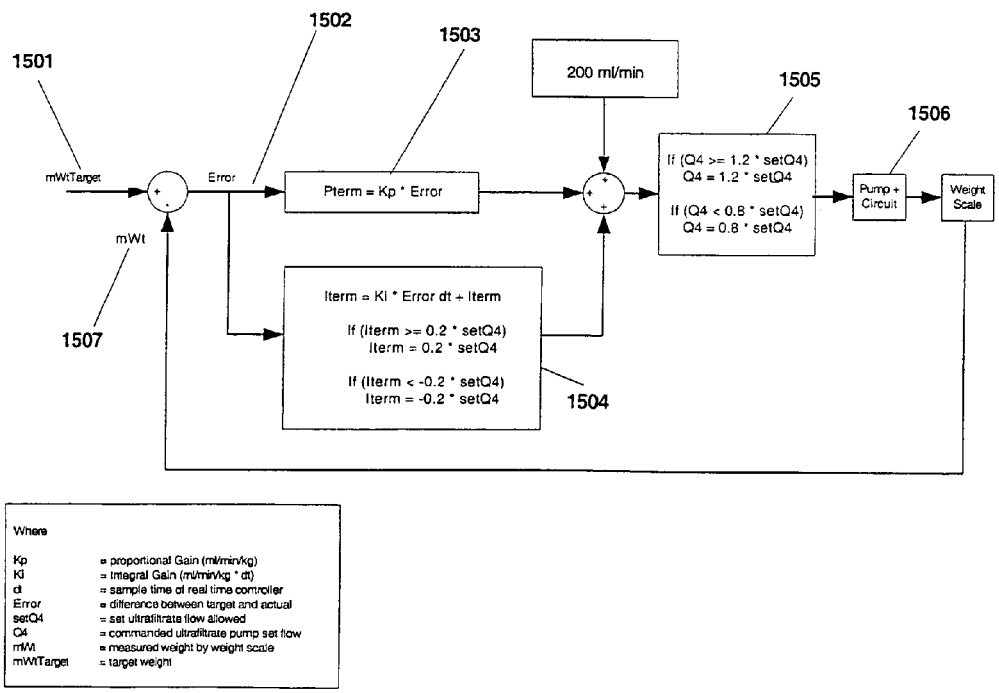
FIG. 15 is a diagram of the control algorithm for matching ultrafiltrate flow with fluid replacement rate.

This algorithm is described in FIG. 15. mWt 1507 is subtracted from WtTarget 1501 to provide an error in tracking 1502. The error is then used to generate an proportional flow rate and an integral flow rate Pterm 1503 and Iterm 1504. The Iterm 1504 is limited to 20% of the maximum flow setQ4 allowed for the ultrafiltration pump which in this case is set to 0.2*200 ml/min=40 ml/min. This limitation of the integral term prevents windup of the integral term. The summed Pterm and Iterm 1505 are also limited to a 20% increase or decrease of the setQ4. The output of the controller Q4 is sent to the motor controller and is updated on a 10 second sample interval. The gains of the controller are adjusted to provide stability over the range of pressure and flows the system operates under. This controller is capable of keeping the mWtTarget to within a gram of its target weight ensuring no clinically significant mismatch between the replacement solution pump and the ultrafiltrate pump.

Ultrafiltration and Replacement Solution Controller:

In practice the rate at which replacement solution is infused and ultrafiltrate is removed will be limited by TMP (Trans Membrane Pressure). As filters are used fouling occurs and the resistance of the filter to ultrafiltrate increases. Thus Kuf decreases. Kuf is measured in terms of ml/hr/mmHg/m². It represents the flow rate possible through the porous filter per hour per mmHg per meter squared, in other word the permeability of the filter. It is sometimes called the flux coefficient of a filter. Thus it is important that the contrast removal system recognize that the filter may foul over time and that the replacement solution and ultrafiltrate rate must be reduced. Since the continuation of contrast removal is paramount and stopping the therapy is very intrusive, maintaining dilution while maintaining safety increases ease of use. This may be achieved with a TMP controller which targets the maximum possible TMP as feedback and adjusts the replacement fluid rate and the ultrafiltrate rate to ensure that the TMP is not exceeded. TMP is calculated as:

$$TMP=((Pp+Pin)/2)-Puf$$

Figure 17:
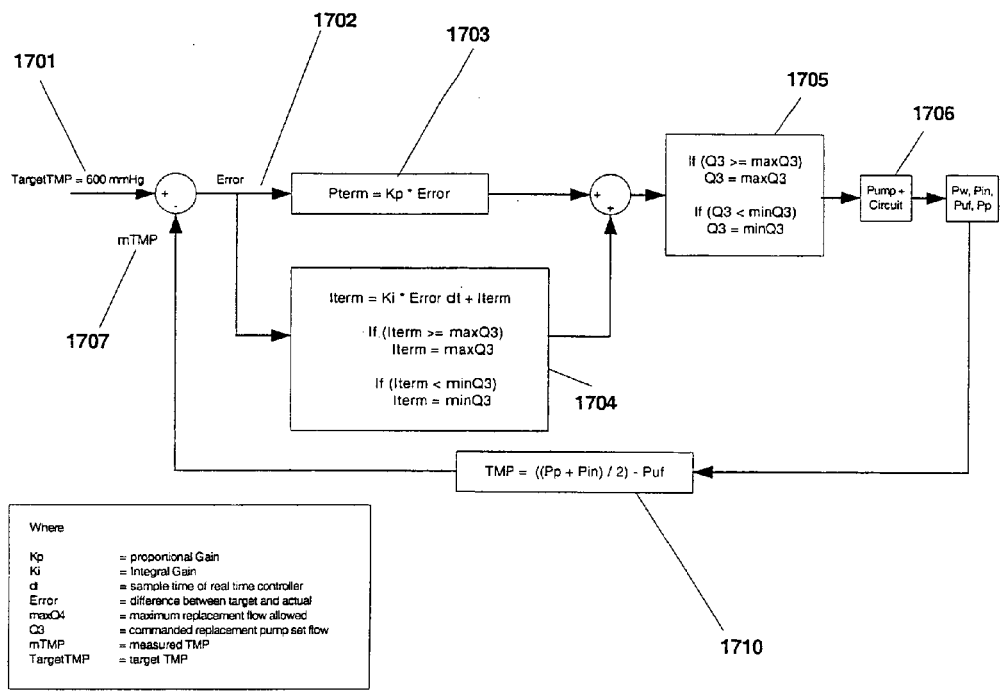
FIG. 17 shows a proportional integral controller.

FIG. 17 shows a PI (proportional Integral) controller for the control of TMP based upon the commanded Q3, the fluid replacement flow rate. When Q3 is adjusted, Q4 and the setmaxQ4 also have to be adjusted described in FIG. 15 to keep the ultrafiltration rate tracking. Both will affect TMP so the gains of Pterm 1703 and Iterm have to be chosen for stability over the full ranges of TMP. A ratio of Q3 to Q4 resulting from the weight scale controller will be maintained at every sample interval so that when Q3 is reduced the compensated rate for Q4 will also be adjusted. Thus for instance the weight scale controller may determine that the set Q4 motor velocity has to be 1.1 times the set Q3 motor velocity to ensure that the weight scale weight remains constant. Thus if Q3 is reduced by 5% the current velocity of t, Q4 must also be reduced by 5% to ensure that the weight scale mWtTarget 1501 FIG. 15 continues to track.

The TMP controller will work to output maxQ3 as long as the TMP is less than the set TargetTMP 1701. The TMP will be measured as shown in 1710. An error signal is generated by the difference between the TargetTMP 1701 and the measured mTMP 1707. This error 1702 is then fed to a proportional 1703 and integral controller 1704. The integral controller limits the windup of flow to the maxQ3 allowed (200 ml/min) and to the minQ3, 0 ml/min 1704 since no reversals are allowed for the replacement solution pump. The outputs of the proportional and integral controllers are then summed and limited 1705 with the same limits as the integral controller 1704. Q3 is then adjusted the controller CPU 305 sending a command to the motor controller 302 (FIG. 3). The TMP controller will only limit the replacement solution rate if TMP is greater than 600 mmHg. Such a controller is possible because the blood pumps are essentially independent of the replacement solution and ultrafiltrate pumps. They are on separate paths and use separate feedback.

In order to main the correct dilution of contrast to less than 5% of its original level 3 times the volume of the filter used will have to be flushed. Thus if the volume of the filter used were 40 ml, the replacement solution will have to displace 120 ml with an equivalent volume of ultrafiltrate removed before the volume of blood within the filter could be considered diluted.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An extracorporeal blood circuit comprising:
a withdrawal conduit connectable to a coronary withdrawal catheter positionable in or proximate to a chamber of a heart of a patient and adapted to receive a flow of blood from the patient;
a withdrawal pump connectable to the withdrawal conduit, wherein a pumping rate of the withdrawal pump determines a blood withdrawal rate from the coronary withdrawal catheter;
at least one filter having an input connectable to the withdrawal conduit and a blood output connectable to an infusion conduit and a filtrate output connectable to a filtrate conduit, wherein the filtrate removed by the at least one filter is a total amount of filtrate removed from the blood by the blood circuit;
a filtrate measurement device to determine a weight of filtrate removed from the blood in the filter;
a replacement fluid conduit adapted to provide a replacement fluid to at least one of the withdrawal conduit, filter and infusion conduit;
a replacement fluid pump connectable to the replacement fluid conduit, wherein a pumping rate of the replacement fluid pump determines a rate at which the replacement fluid flows into the blood flowing through the blood circuit;
a controller for regulating the pumping rate of the replacement fluid pump such that the rate of the replacement fluid provides an amount of replacement fluid to the at least one of the withdrawal conduit, filter and infusion conduit, wherein the controller determines a total amount of filtrate removed based on the weight of the filtrate removed from the blood, and adjusts the pumping rate such that the amount of infused replacement fluid is commensurate with the amount of filtrate removed throughout the extracorporeal blood circuit while the replacement fluid is being added to the at least one of the withdrawal conduit, filter and infusion conduit, and
the infusion conduit connectable to a catheter insertable into the patient to infuse filtered blood and the replacement fluid to the patient while the filtrate is being removed and the blood flows into the withdrawal catheter.

2. An extracorporeal blood circuit as in claim 1 wherein the filtrate measurement device is a weight scale connectable to a filtrate collection bag.

3. An extracorporeal blood circuit as in claim 2 wherein the weight scale is connectable to a bag containing the replacement fluid.

4. An extracorporeal blood circuit as in claim 3 wherein the controller regulates at least one of the pumping rate of the replacement fluid pump and the pumping rate of the withdrawal pump by maintaining a combined weight of the bag containing the replacement fluid and the filtrate collection bag within a predefined weight range.

5. The extracorporeal blood circuit as in claim 1 wherein the chamber is the coronary sinus and the coronary withdrawal catheter occludes the coronary sinus when positioned in or proximate to the heart.

6. The extracorporeal blood circuit as in claim 5 wherein the coronary withdrawal catheter includes an expandable member to occludes the coronary sinus.

7. A method for infusing a supplemental fluid into a patient and removing filtrate from the patient using an extracorporeal blood circuit, the method comprising:
withdrawing blood from the patient and into the extracorporeal blood circuit;

pumping the withdrawn blood through the extracorporeal blood circuit at a pumping rate which determines a blood withdrawal rate from the patient;

filtering the withdrawn blood in the extracorporeal blood circuit to remove filtrate from the blood;

measuring a weight of filtrate removed from the blood, wherein the measured weight of filtrate represents a total weight of all filtrate removed from the blood in the blood circuit;

adding a supplemental fluid to the withdrawn blood at an infusion rate;

controlling at least one of a filtrate removal rate of the filtrate being removed from the blood throughout the extracorporeal blood circuit and the infusion rate of the supplemental fluid so that the total weight of the removed filtrate is commensurate with a weight of the supplemental fluid infused into the withdrawn blood, and infusing into the patient the filtered withdrawn blood and the supplemental fluid added to the withdrawn blood, while blood is being withdrawn to the extracorporeal blood circuit.

8. A method as in claim 7 wherein the step of filtering is performed with a blood filter having an input connected to a blood withdrawal conduit, a blood output connected to a blood infusion conduit and a filtrate output connected to a filtrate conduit.

9. A method as in claim 7 wherein the supplemental fluid is infused after the blood has been filtered.

10. A method as in claim 7 wherein the measuring the amount of the filtrate includes weighing a bag containing the filtrate and the controlling step includes comparing a weight of the bag containing the filtrate to a weight of the bag containing the supplemental fluid, and adjusting the infusion rate or the removal rate to maintain within a predefined range the combined weight of the bag containing the supplemental fluid and the bag containing the filtrate.

11. A method as in claim 10 wherein the measuring the amount of the filtrate includes weighing together a bag containing the filtrate and a bag containing the fluid supplementation.

12. An extracorporeal blood circuit comprising:

a withdrawal conduit connectable to a coronary withdrawal catheter positionable in or proximate to a chamber of a heart of a patient;

a withdrawal pump connectable to the withdrawal conduit, wherein a pumping rate of the withdrawal pump determines a blood withdrawal rate from the coronary withdrawal catheter;

a filter having an input connected to the withdrawal conduit and a blood output connected to an infusion conduit and a filtrate output connected to a filtrate conduit;

a filtrate measurement device to determine a weight of a total amount of filtrate removed from the blood in the filter and by the blood circuit;

a replacement fluid conduit providing a replacement fluid to at least one of the withdrawal conduit, the filter and the infusion conduit;

a filtrate pump connectable to the filtrate conduit, wherein a pumping rate of the filtrate pump determines a rate at which the filtrate is withdrawn from the blood flowing through the blood circuit;

a controller programmed to regulate the pumping rate of the filtrate pump such that the rate at which filtrate is withdrawn provides an amount of filtrate having a filtrate weight as measured by the filtrate measurement device which corresponds to a weight of the replacement fluid infused into the withdrawn blood throughout the extracorporeal blood circuit, and the infusion conduit connectable to a catheter insertable into the patient to infuse filtered blood and the replacement fluid while blood is being withdrawn into the withdrawal conduit.

13. An extracorporeal blood circuit as in claim 12 wherein the filtrate measurement device is a weight scale connectable to a filtrate collection bag.

14. An extracorporeal blood circuit as in claim 13 wherein the weight scale is connectable to a bag containing the replacement fluid.

15. An extracorporeal blood circuit as in claim 14 wherein the controller regulates at least one of the pumping rate of a replacement fluid pump and the pumping rate of the withdrawal pump by maintaining a combined weight of the bag containing the replacement fluid and the filtrate collection bag within a predefined weight range.

16. The extracorporeal blood circuit as in claim 12 wherein the chamber is the coronary sinus and the coronary withdrawal catheter occludes the coronary sinus when positioned in or proximate to the heart.

17. The extracorporeal blood circuit as in claim 16 wherein the coronary withdrawal catheter includes an expandable member to occlude the coronary sinus.

* * * * *